US012296030B2

United States Patent
Hogg et al.

(10) Patent No.: US 12,296,030 B2
(45) Date of Patent: May 13, 2025

(54) CONJUGATES AND THEIR USE AS IMAGING AGENTS

(71) Applicants: Centenary Institute of Cancer Medicine and Cell Biology, Camperdown (AU); University of Sydney, Sydney (AU)

(72) Inventors: Philip Hogg, Malabar (AU); Ivan Ho Shon, Strathfield (AU)

(73) Assignees: CENTENARY INSTITUTE OF CANCER MEDICINE AND CELL BIOLOGY (AU); UNIVERSITY OF SYDNEY (AU)

( * ) Notice: Subject to any disclaimer, the term of this patent is extended or adjusted under 35 U.S.C. 154(b) by 0 days.

(21) Appl. No.: 18/452,312

(22) Filed: Aug. 18, 2023

(65) Prior Publication Data

US 2024/0009330 A1   Jan. 11, 2024

Related U.S. Application Data

(63) Continuation of application No. 17/594,325, filed as application No. PCT/AU2020/050359 on Apr. 9, 2020.

(30) Foreign Application Priority Data

Apr. 12, 2019   (AU) .................................. 2019901277

(51) Int. Cl.
| | |
|---|---|
| *A61K 51/04* | (2006.01) |
| *A61P 35/00* | (2006.01) |
| *C07F 9/78* | (2006.01) |

(52) U.S. Cl.
CPC .......... *A61K 51/0497* (2013.01); *A61P 35/00* (2018.01); *C07F 9/78* (2013.01)

(58) Field of Classification Search
CPC ......... A61K 51/0497; A61P 35/00; C07F 9/78
USPC ...................................................... 424/1.65
See application file for complete search history.

(56) References Cited

FOREIGN PATENT DOCUMENTS

| WO | WO2001/021628 A1 | 3/2001 | |
|---|---|---|---|
| WO | WO2002/074305 A1 | 9/2002 | |
| WO | WO2003/003011 A1 | 1/2003 | |
| WO | WO2003/039564 A1 | 5/2003 | |
| WO | WO-03039564 A1 * | 5/2003 | ............ A61K 33/36 |
| WO | WO2004/042079 A1 | 5/2004 | |
| WO | WO2008/052279 A1 | 5/2008 | |
| WO | WO2009/043114 A1 | 4/2009 | |
| WO | WO2010/036837 A1 | 4/2010 | |
| WO | WO2016/061618 A1 | 4/2016 | |
| WO | WO2016/201481 A1 | 12/2016 | |
| WO | WO2020/206503 A9 | 10/2020 | |
| WO | WO2022/077068 A1 | 4/2022 | |
| WO | WO2023/060317 A1 | 4/2023 | |

OTHER PUBLICATIONS

Mueller et al. Bioconjugate Chem. 2012, 23, 1712-1717. (Year: 2012).*
Kumar et al. Mol. Imaging Biol. 2019, 21, 130-139. (Year: 2019).*
Dilda et al., "Para to Ortho Repositioning of the Arsenical Moiety of the Angiogenesis Inhibitor 4-(N-(S-Glutathionylacetyl)Amino) Phenylarsenoxide Results in a Markedly Increased Cellular Accumulation and Antiproliferative Activity", *Cancer Research* 65(24):11729-11734 (2005).
Dilda et al., "Metabolism of the Tumor Angiogenesis Inhibitor 4-(N-(S-Glutathionylacetyl)amino)phenylarsonous Acid", *Journal of Biological Chemistry* 283(51):35428-35434 (2008).
Don et al., "A peptide trivalent arsenical inhibits tumor angiogenesis by perturbing mitochondrial function in angiogenic endothelial cells", *Cancer Cell* 3(5):497-509 (2003).
Dumont et al., "Novel $^{64}$Cu- and $^{68}$GA-Labeled RGD Conjugates Show Improved PET Imaging of $\alpha_v\beta_3$ Integrin Expression and Facile Radiosynthesis", *The Journal of Nuclear Medicine* 52(8):1276-1284 (2011).

(Continued)

*Primary Examiner* — Michael G. Hartley
*Assistant Examiner* — Sean R Donohue
(74) *Attorney, Agent, or Firm* — LATHROP GPM LLP; Brian C. Trinque

(57) ABSTRACT

The invention relates to compounds according to Formula (I):

wherein A is —As(OH)$_2$ or an arsenoxide equivalent group; each of R$_1$, R$_2$, R$_3$ and R$_4$ is independently selected from H, X, OH, NH$_2$, CO, SCN, —CH$_2$NH, —NHCOCH$_3$, —NHCOCH$_2$X or NO, and X is a halogen; R$_5$ is —NHCH$_2$COOH, OH or OR$_6$, wherein R$_6$ is a C$_{1-5}$ straight or branched alkyl group; and Z is a radioisotope with a half-life of less than 4 days, or a pharmaceutically acceptable salt, ester, prodrug or solvate thereof, uses of said compounds, and methods of preparing said compounds. The invention also relates to diagnostic methods utilizing said compounds.

19 Claims, 18 Drawing Sheets

(56) References Cited

OTHER PUBLICATIONS

Elliott et al., "Pharmaceutical development of the novel arsenical based cancer therapeutic GSAO for Phase I clinical trial", *International Journal of Pharmaceutics* 426:67-75 (2012).
Ho Shon et al. "Comparison of a novel Hsp90 ligand radiolabelled with Indium-111 and Gallium-67 for imaging of cell death and dosimetry estimations", *European Journal of Nuclear Medicine and Molecular Imaging*, vol. 39, Suppl. 2, pp. S215-S216, Abstract No. OP309 (2012).
Ho Shon et al., "Preparation of a Dithiol-Reactive Probe for PET Imaging of Cell Death", *Methods in Molecular Biology* 1967:295-304 (2019).
Ho Shon et al. "Biodistribution and imaging of an hsp90 ligand labelled with $^{111}$In and $^{67}$Ga for imaging of cell death", *EJNMMI Research* 10(1):4 (2020).
Ho Shon et al., "A first in human study of Cell Death Indicator positron emission tomography (CDI-PET)-interim analysis", *Journal of Nuclear Medicine*, (May 2020) vol. 61, Supp. Supplement 1, Abstract No. 344, 2020 Annual Meeting of the Society of Nuclear Medicine and Molecular Imaging, SNMMI 2020, New Orleans, LA, United States, Jun. 13-16, 2020, Poster.
Ho Shon et al., "Preclinical assessment of [$^{68}$Ga]Ga-Cell Death Indicator (CDI): a novel hsp90 ligand for positron emission tomography of cell death", *Current Radiopharmaceuticals* (2021).
Horsley et al., "A phase 1 trial of intravenous 4-(N-(S-glutathionylacetyl)amino) phenylarsenoxide (GSAO) in patients with advanced solid tumours", *Cancer Chemotherapy and Pharmacology* 72(6):1343-1352 (2013).
International Search Report for PCT/AU2020/050359 dated Jun. 19, 2020.
International Search Report and Written Opinion for International Application No. PCT/AU2021/051203, mailed Dec. 9, 2021, 11 pages.
International Search Report and Written Opinion for International Application No. PCT/AU2022/051236, mailed Dec. 20, 2022, 13 pages.
Kuan et al., "Noninvasive Imaging of Dead and Dying Cells by Novel Organo Arsenicals", *Journal of Labelled Compounds and Radiopharmaceuticals* 52(Suppl. 1):S38, (2009).
Makris et al., "Somatostatin receptor targeting with hydrophilic [$^{99m}$Tc/$^{186}$Re]Tc/Re-tricarbonyl NODAGA and NOTA complexes", *Nuclear Medicine and Biology* 71:39-46 (2019).
Marciniak et al., Somatostatin analogues labeled with copper radioisotopes: current status, *Journal of Radioanalytical and Nuclear Chemistry* 313:279-289 (2017).
Massamiri et al., Characterisation of a small, synthetic imaging agent for dying and dead tumour cells, *Cancer Microenvironment* 2(Suppl. 1):S185, Abstract No. 181 (2009).
Nyiranshuti et al., "PET imaging using an apoptosis probe, [Cu-64]-NODAGA-Duramycin, for therapy assessment in solid tumors", *The Journal of Nuclear Medicine* 59(2):366, Abstract No. 47 (2018).
Pandurangi et al. "Relevance of noninvasive imaging of dead and dying cells in adverse cardiovascular and oncological situations", *Journal of Labelled Compounds and Radiopharmaceuticals*, vol. 52, Suppl. 1, p. S411, Abstract No. P311 (2009).
Park et al., "Noninvasive Imaging of Cell Death Using an Hsp90 Ligand", *Journal of the American Chemical Society* 133(9):2832-2835 (2011).
Park et al., "Noninvasive Imaging of Cell Death Using an Hsp90 Ligand", *Journal of the American Chemical Society* 133(9):2832-2835 (2011), Supporting Information.
Park et al., "Non-invasive Imaging of tumor cell death using a Hsp90 ligand", *Cancer Research*, (Apr. 15, 2011) vol. 71, No. 8, Suppl. 1, Abstract No. 5287, 102nd Annual Meeting of the American Association for Cancer Research, AACR 2011, Orlando, FL, United States Apr. 2-6, 2011.
Park et al., "Optical Imaging of Treatment-Related Tumor Cell Death Using a Heat Shock Protein-90 Alkylator", *Molecular Pharmaceutics* 10(10): 3882-3891 (2013).
Rylova et al., "Does Imaging $\alpha_v\beta_3$ Integrin Expression with PET Detect Changes in Angiogenesis During Bevacizumab Therapy?", *The Journal of Nuclear Medicine* 55(11):1878-1884 (2014).
Sarko et al., "Bifunctional Chelators in the Design and Application of Radiopharmaceuticals for Oncological Diseases", *Current Medicinal Chemistry* 19:2667-2688 (2012).
Spang et al., "Bifunctional Gallium-68 Chelators: Past, Present, and Future", *Seminars in Nuclear Medicine* 46:373-394 (2016).
Sun et al., "Preclinical Study on GRPR-Targeted $^{68}$Ga-Probes for PET Imaging of Prostate Cancer", *Bioconjugate Chemistry* 27(8):1857-1864 (2016).
Svoboda et al., "Protection or Sensitization by Thiols or Ascorbate in Irradiated Solutions of DNA or Deoxyguanosine", *Radiation Research* 151:605-616 (1999).
Tahara et al., "Noninvasive Molecular Imaging of Cell Death in Myocardial Infarction using $^{111}$In-GSAO", *Scientific Reports* vol. 4, Article No. 6826 (2014).
Tamba, "Role of Thiols in Radioprotection: Radiation Chemical Aspects", *Zeitschrift für Naturforschung C: A Journal of Biosciences* 44(9-10):857-862 (1989).
Xie et al., "Optical imaging of cell death in traumatic brain injury using a heat shock protein-90 alkylator", *Cell Death and Disease* 4, e473 (2013); doi:10.1038/cddis.2012.207.
Chakrabarti et al., "Prevention of Radiolysis of Monoclonal Antibody during Labeling", *The Journal of Nuclear Medine* 37(8):1384-1388 (1996).
Kalinina et al., "Role of Glutathione, Glutathione Transferase, and Gluxtaredoxin in Regulation of Redox-Dependent Process", *Biochemistry* (Moscow) 79(13):1562-1583 (2014).
Vondeneev et al., "Targeted radionuclide therapy: current status and prospects", *Genes & Cells* vol. X, No. 1, pp. 23-29 (2015).

* cited by examiner 0 min 8 min 17 min 28 min 42 min 60 min 120 min 178 min

FDG PET CT 0 min   8 min   17 min   28 min 42 min   60 min   120 min   178 min

FDG PET CT

CONJUGATES AND THEIR USE AS IMAGING AGENTS

RELATED APPLICATIONS

This application is a continuation of U.S. application Ser. No. 17/594,325, filed on Oct. 11, 2021, which application is a 35 U.S.C. § 371 filing of International Application No. PCT/AU2020/050359, filed Apr. 9, 2020, which application claims priority to Australian Patent Application No. 2019901277, filed Apr. 12, 2019. The entire contents of these applications are herein incorporated by reference in their entireties.

TECHNICAL FIELD

The present invention broadly relates to a radiolabelled conjugate according to Formula (I) defined herein, and a compound according to Formula (II) defined herein. The present invention further relates to the use of such radiolabelled conjugates in imaging of cell death, diagnosis and treatment of conditions associated with cell death, and methods of producing such radiolabelled conjugates.

BACKGROUND OF THE INVENTION

Cell death plays an integral role in cell turnover. An imbalance of cell death, characterised by a marked increase or decrease of cell death relative to cell regeneration, is often associated with disease. For example, excessive cell death is characteristic of vascular disorders, neurodegenerative diseases, myelodysplastic syndromes, ischaemia/reperfusion injury, organ transplant rejection, and neoplastic conditions including tumours and cancers, among others. In particular, cancer results from imbalance between rates of cellular proliferation and survival in a tissue.

Visualisation of cell death therefore has the potential to be a highly useful tool in the diagnosis and treatment of numerous conditions associated with abnormal levels of cell death, as well as assessment and monitoring cell death, for example during drug development and testing of tissue toxicity of a given substance. In oncology, for example, where successful treatment controls cancer cell growth by inhibiting cellular proliferation and/or promoting cell death, the ability to directly image cell death as a means of assessing response to treatment is highly desirable but not available. Presently, imaging for assessment of treatment response in oncology indirectly assesses cell death by either a reduction in tumour size (by anatomic techniques such as computerised tomography (CT) and magnetic resonance imaging (MRI)) or by a reduction in metabolic activity (most usually glucose metabolic activity) by positron emission tomography (PET). Although these techniques are widely and routinely used in oncology, they indirectly assess cell death, and are thus subject to both false positive and false negative findings. In addition, these techniques do not assess cell death in real time and typically are not performed until at least a number of weeks after commencement of therapy (e.g. positron emission tomography with 2-fluoro-2-deoxyglucose (FDG PET/CT) is usually not performed until after two cycles of chemotherapy—typically 6 to 8 weeks after commencement of treatment). Further, changes in tumour size measured by CT, such as using Response Evaluation Criteria in Solid Tumours (RECIST 1.1), are often but not always associated with response to therapy. Reduction in tumour size is slow to occur following commencement of treatment (often taking several months) and in some cases may not occur at all despite a response to therapy. Limited attempts have been made to directly image cell death, such as using derivatives of Annexin V and radiolabelled caspase 3/7 inhibitors, however these have been hampered by complex and expensive production, poor biodistribution, particularly with high physiologic uptake in blood and normal tissues/organs, especially the liver and bowel, poor tissue penetration and an inability to reliably detect tumour cell death in response to treatment. In view of the absence of methods to reliably detect tumour cell death in response to therapy in vivo, the kinetics of cell death are poorly understood.

For these reasons, a method to directly assess tumour cell death in near real-time (within days of commencement of treatment) would potentially be highly beneficial in clinical and research oncology.

A particularly advantageous imaging agent would allow rapid serial imaging commensurate with the time course of cell death following, for example, administration of a cancer treatment which causes tumour cell death. Such an imaging agent would allow changes in cell death to be visualised on a biologically and clinically relevant timescale. It is thus desirable to provide convenient and sensitive imaging agents which allow non-invasive effective and accurate visualisation of cell death, in a manner and time frame suitable for use in the diagnosis and treatment of disease.

SUMMARY OF THE INVENTION

According to a first aspect, the present disclosure provides a compound according to Formula (I)

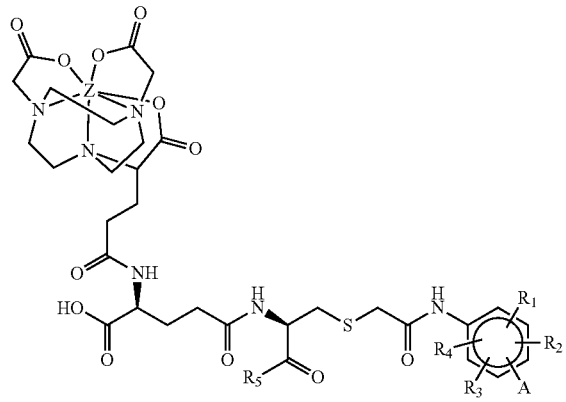

Formula (I)

wherein A is —As(OH)$_2$ or an arsenoxide equivalent group; each of R$_1$, R$_2$, R$_3$ and R$_4$ is independently selected from H, X, OH, NH$_2$, CO, SCN, —CH$_2$NH, —NHCOCH$_3$, —NHCOCH$_2$X or NO, and X is a halogen; R$_5$ is —NHCH$_2$COOH, OH or OR$_6$, wherein R$_6$ is a C$_{1-5}$ straight or branched alkyl group; and Z is a radioisotope with a half-life of less than 4 days, or a pharmaceutically acceptable salt, ester, prodrug or solvate thereof.

Compounds according to the present disclosure are useful for imaging cell death in vitro and in vivo. The compounds allow accurate, sensitive and non-invasive detection and measurement of cell death. In particular, such compounds find use in diagnosing, monitoring, and assessing treatment of various disorders and conditions wherein cell death is relevant factor. Radiolabelled compounds of the present invention can be readily synthesised for use in vivo, show favourable biodistribution, imaging characteristics and radiation dosimetry and allow visualisation of cell death on a clinically relevant timescale due to the half-life of the radioisotope used.

In some embodiments, each of $R_1$, $R_2$, $R_3$ and $R_4$ are H. In some embodiments, $R_5$ is —NHCH$_2$COOH. In some embodiments, the compound is a compound according to Formula (Ia)

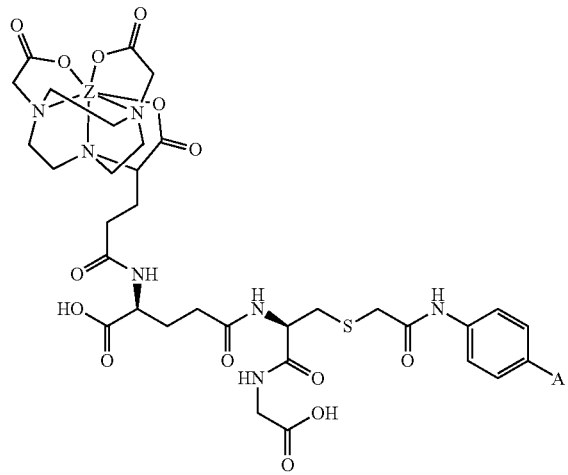

Formula (Ia)

wherein A is as defined above, or a pharmaceutically acceptable salt, ester, prodrug or solvate thereof.

In some embodiments, Z has a half-life of less than 1 day. In some embodiments, Z has a half-life of less than 4 hours. In some embodiments, Z has a half-life of less than 2 hours. In some embodiments, Z is $^{68}$Ga.

$^{68}$Ga has a half-life of 68 minutes, meaning it is particularly useful for visualisation of cell death by way of PET; the use of such a short-lives positron emitting radioisotope allows frequent serial and quantitative imaging.

A particularly preferred compound is a compound according to Formula (I) wherein Z is $^{68}$Ga, $R_1$-$R_4$ are H, $R_5$ is —NHCH$_2$COOH, and A is As(OH)$_2$. Such an embodiment provides the above-mentioned advantages of being readily synthesised, being synthesised from readily available and affordable starting materials, exhibiting good biodistribution, low normal organ uptake, advantageous imaging characteristics, favourable radiation dosimetry and a short half-life suitable for sequential repeated imaging by Positron Emission Tomography.

The present disclosure provides the compounds according to the first aspect for use as imaging agents, for example for use as imaging agents in positron emission tomography. In particular embodiments, the present disclosure provides the compounds according to the first aspect for use in visualising cell death.

According to a second aspect, the present disclosure provides a pharmaceutical composition comprising the compound according to the first aspect together with a pharmaceutically acceptable carrier, excipient, diluent, vehicle and/or adjuvant.

According to a third aspect, the present disclosure provides a compound according to Formula (II)

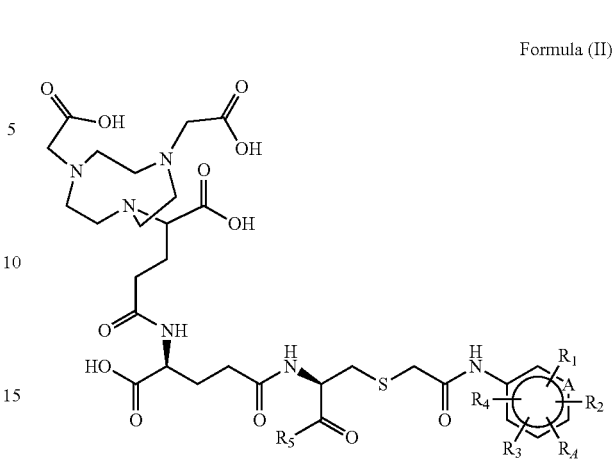

Formula (II)

wherein A is —As(OH)$_2$ or an arsenoxide equivalent group; each of $R_1$, $R_2$, $R_3$ and $R_4$ is independently selected from H, X, OH, NH$_2$, CO, SCN, —CH$_2$NH, —NHCOCH$_3$, —NHCOCH$_2$X or NO, and X is a halogen; $R_5$ is —NHCH$_2$COOH, OH or OR$_6$, wherein $R_6$ is a C$_{1-5}$ straight or branched alkyl group; or a pharmaceutically acceptable salt, ester, prodrug or solvate thereof. Such compounds are useful in the preparation of the compounds according to the first aspect as described above, and may be converted to compounds of Formula (I) by radiolabelling with a radioisotope.

In some embodiments, each of $R_1$, $R_2$, $R_3$ and $R_4$ are H. In some embodiments, $R_5$ is —NHCH$_2$COOH. In some embodiments, the compound according to Formula (II) is a compound according to Formula (IIa)

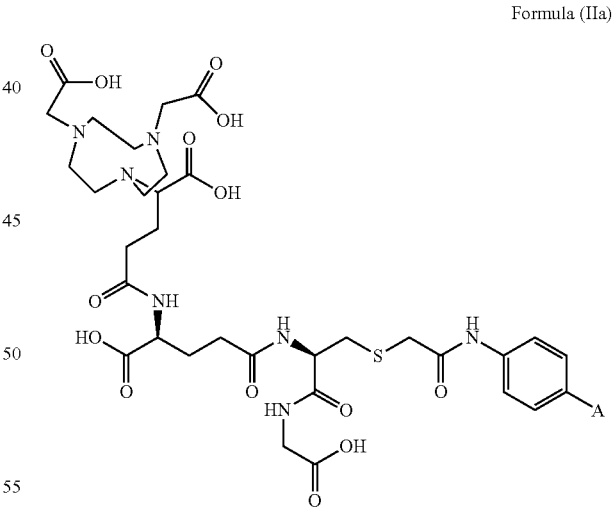

Formula (IIa)

wherein A is as defined for Formula (II); or a pharmaceutically acceptable salt, ester, prodrug or solvate thereof.

According to a fourth aspect, the present disclosure provides use of a compound according to the first aspect as an imaging agent. The imaging agent may be used in positron emission tomography. The imaging agent may be used to visualise cell death.

According to a fifth aspect, the present disclosure provides a compound of the first aspect for use in therapy. The compound may be for use in the treatment of a condition associated with changes in cell death and/or treatment of which results in a change in cell death.

According to a sixth aspect, the present disclosure provides a compound of the first aspect for use in in vivo diagnostics. The compound may be for use in the diagnosis of a condition associated with changes in cell death and/or treatment of which results in a change in cell death.

The compound for use according to the fifth or sixth aspect may be for use in the treatment or diagnosis of a neoplastic condition or an autoimmune condition. The neoplastic condition may be a tumour. The neoplastic condition may be cancer.

According to a seventh aspect, the present disclosure provides a method of diagnosing or treating a condition in a subject wherein the condition is associated with changes in cell death and/or treatment of the condition results in a change in cell death, or visualising cell death in a subject comprising administering an effective amount of a compound according to the first aspect. In some embodiments, the condition is a neoplastic condition or an autoimmune condition. The method may further comprise conducting positron-emission tomography on the subject following administration of a compound according to the first aspect. Multiple positron-emission tomography images may be collected following administration of the compound according to the first aspect. In some embodiments, the collection of multiple images may allow more accurate and quantifiable assessments of cell death to be made, since differences in cell death over a given period may be determined rather than absolute values.

The compound according to the first aspect may be administered intravenously.

In methods according to the seventh aspect, the neoplastic condition may be a tumour. The neoplastic condition may be cancer.

According to an eighth aspect, the present disclosure provides a method of assessing response of a subject to a therapy intended to cause a change in level of cell death, comprising: administering the therapy; administering a compound according to the first aspect; and visualising cell death. In some embodiments, cell death is visualised by conducting positron emission tomography on the subject. In some embodiments, the therapy is chemotherapy, radiotherapy, targeted therapy or immunotherapy, or combinations thereof.

According to a ninth aspect, the present disclosure provides a process for preparing a compound according to the first aspect wherein Z is $^{68}$Ga, comprising eluting $^{68}$Ga onto a strong cation exchange column; and eluting the strong cation exchange column into a mixture comprising a compound according to Formula (II) and a buffer, wherein the buffer has a pH of about 4.5.

BRIEF DESCRIPTION OF THE DRAWINGS

Exemplary embodiments of the present disclosure are described herein, by way of non-limiting example only, with reference to the following drawings.

DETAILED DESCRIPTION OF THE INVENTION

Figure 1:
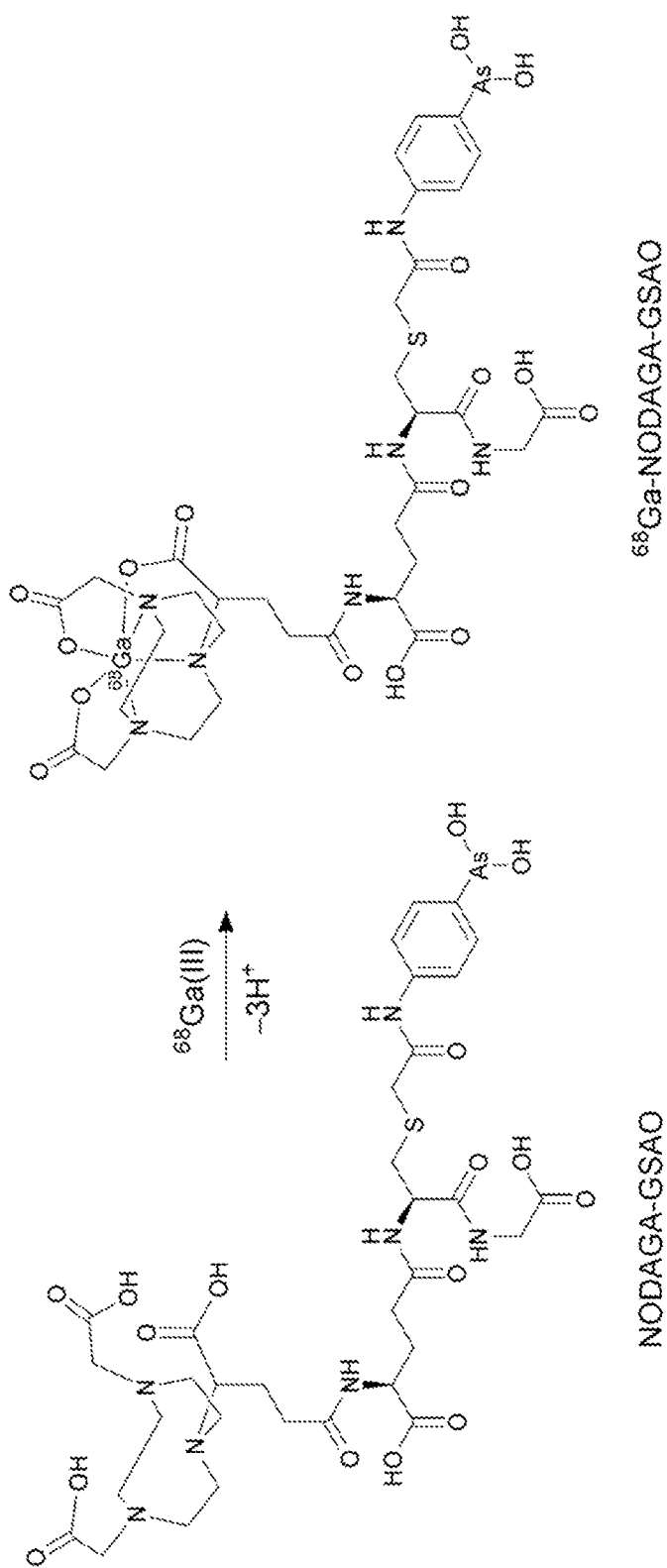
FIG. 1 shows the structures of NODAGA-GSAO and $^{68}$Ga-NODAGA-GSAO.

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, typical methods and materials are described.

Throughout this specification, unless the context requires otherwise, the word "comprise", or variations such as "comprises" or"comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

In the context of this specification, the terms "a" and "an" refer to one or to more than one (i.e. to at least one) of the grammatical object of the article. By way of example, "an element" means one element or more than one element.

In the context of this specification, the term "about" is understood to refer to a range of numbers that a person of skill in the art would consider equivalent to the recited value in the context of achieving the same function or result.

In the context of this specification, reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein, the term "and/or" means "and" or "or" or both.

The term "subject" as used herein refers to any mammal, including, but not limited to, livestock and other farm animals (such as cattle, goats, sheep, horses, pigs and chickens), performance animals (such as racehorses), companion animals (such as cats and dogs), laboratory test animals and humans. Typically the subject is a human.

As used herein the terms "treating", "treatment", "treating", "reduce", "reducing", "prevent" "preventing" and "prevention" and the like refer to any and all applications which remedy, or otherwise hinder, retard, or reverse the progression of, an infection or disease or at least one symptom of an infection or disease, including reducing the severity of an infection or disease. Thus, the terms "treat", "treating", "treatment", do not necessarily imply that a subject is treated until complete elimination of the infection or recovery from a disease. Similarly, the terms "prevent", "preventing", "prevention" and the like refer to any and all applications that prevent the establishment of an infection or disease or otherwise delay the onset of an infection or disease.

The term "optionally" is used herein to mean that the subsequently described feature may or may not be present or that the subsequently described event or circumstance may or may not occur. Hence the specification will be understood to include and encompass embodiments in which the feature is present and embodiments in which the feature is not present, and embodiments in which the event or circumstance occurs as well as embodiments in which it does not.

As used herein the terms "effective amount" and "effective dose" include within their meaning a non-toxic but sufficient amount or dose of a compound to provide the desired effect. The exact amount or dose required will vary from subject to subject depending on factors such as the species being treated, the age and general condition of the subject, the severity of the condition being treated, the particular compound being administered and the mode of administration and so forth. Thus, it is not possible to specify an exact "effective amount" or "effective dose". However, for any given case, an appropriate "effective amount" or "effective dose" may be determined by one of ordinary skill in the art using only routine experimentation.

In the context of the present specification, the term "arsenoxide" refers to the group —As=O. The groups written —As=O and —As(OH)$_2$ are to be considered synonymous.

As used herein, the term "arsenoxide equivalent" refers to any dithiol reactive species that shows essentially the same affinity towards dithiols as —As=O or As(OH)$_2$, and the term includes, for example, groups comprising a transition element, and any trivalent arsenical that is either hydrolysed to —As=O or —As(OH)$_2$ when dissolved in aqueous medium (such as cell culture buffers and the fluids contained in the organism being treated). Typically, arsenoxide equivalent includes dithiol reactive entities, such as As, Ge, Sn and Sb species. Arsenoxide equivalents are expected to exhibit identical or substantially identical activity to that of the corresponding arsenoxide.

The term "bifunctional chelator" refers to a chemical moiety which comprises a chelating moiety capable of binding a metal or other ion, for example a radionuclide, as well as a chemically reactive functional group for attachment to a further chemical entity. In the context of the present application, the term "bifunctional chelator" refers to both the relevant chemical compound before chelation with a metal or other ion and/or before reaction at the reactive functional group, as well as once chelated to a metal or other ion and/or attached to a further chemical entity by way of the reactive functional group, the relevant definition being readily apparent from context. When not chelating a metal or other ion, a bifunctional chelator is suitable for chelating a metal or other ion.

The terms "$C_1$-$C_5$-alkyl", or the like, as used herein, refer to saturated, straight- or branched-chain hydrocarbon radicals containing between one and three, one and six or one and twelve carbon atoms, respectively. Examples of $C_1$-$C_5$-alkyl radicals include but are not limited to methyl, ethyl, propyl, isopropyl, n-butyl, sec-butyl, isobutyl, tert-butyl, pentyl, isopentyl and neopentyl.

By "pharmaceutically acceptable salt" it is meant those salts which, within the scope of sound medical judgement, are suitable for use in contact with the tissues of humans and lower animals without undue toxicity, irritation, allergic response and the like, and are commensurate with a reasonable benefit/risk ratio. Reference to a compound herein shall be understood to include its pharmaceutically acceptable salts unless specified otherwise or otherwise understood from context.

Provided herein are compounds according to Formula (X)

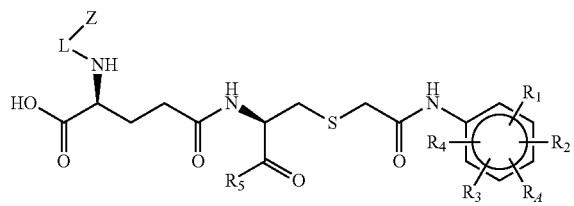

Formula (X)

wherein A is —As(OH)$_2$ or an arsenoxide equivalent group; each of $R_1$, $R_2$, $R_3$ and $R_4$ is independently selected from H, X, OH, NH$_2$, CO, SCN, —CH$_2$NH, —NHCOCH$_3$, —NHCOCH$_2$X or NO, and X is a halogen; $R_5$ is —NHCH$_2$COOH, OH or OR$_6$, wherein R$_6$ is a $C_{1-5}$ straight or branched alkyl group; Z is a radioisotope with a half-life of less than 4 days; and L is a bifunctional chelator chelating Z; or a pharmaceutically acceptable salt, ester, prodrug or solvate thereof.

In some embodiments, the compound according to Formula (X) is a compound according to Formula (Xa), or pharmaceutically acceptable salt, ester, prodrug or solvate thereof.

Formula (Xa)

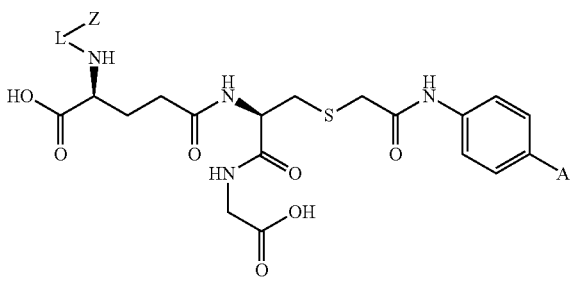

In preferred embodiments, Z is $^{68}$Ga. In preferred embodiments, L is a bifunctional chelator known to chelate a radioisotope having a half-life of less than 4 days, in particular $^{68}$Ga, at room temperature and with a high affinity.

The present disclosure provides a compound according to Formula (I)

Formula (I)

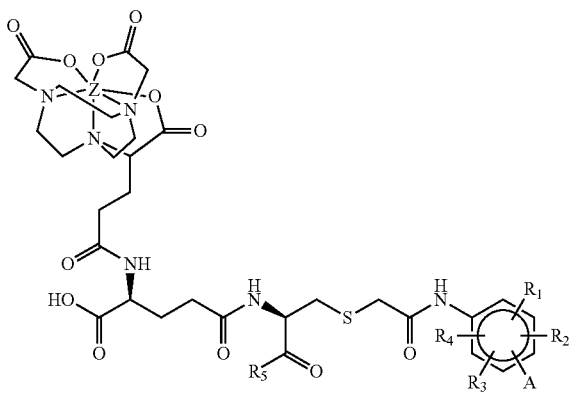

wherein A is —As(OH)$_2$ or an arsenoxide equivalent group; each of $R_1$, $R_2$, $R_3$ and $R_4$ is independently selected from H, X, OH, NH$_2$, CO, SCN, —CH$_2$NH, —NHCOCH$_3$, —NHCOCH$_2$X or NO, and X is a halogen; $R_5$ is —NHCH$_2$COOH, OH or OR$_6$, wherein R$_6$ is a C$_{1-5}$ straight or branched alkyl group; and Z is a radioisotope with a half-life of less than 4 days, or a pharmaceutically acceptable salt, ester, prodrug or solvate thereof. In some preferred embodiments, each of $R_1$, $R_2$, $R_3$ and $R_4$ are H. In some preferred embodiments, $R_5$ is —NHCH$_2$COOH. In particular preferred embodiment, the compound is a compound according to Formula (Ia):

Formula I(a)

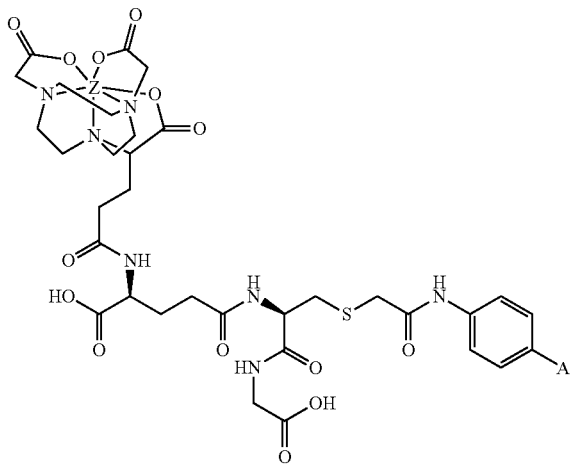

or a pharmaceutically acceptable salt, ester, prodrug or solvate thereof. In preferred embodiments, A is an arsenoxide group As(OH)$_2$.

In compounds suitable for use in the present invention, the arsenoxide group (—As(OH)$_2$) can typically be replaced by an arsenoxide equivalent.

Such compounds are based on 4-(N—(S-glutathionylacetyl)amino)phenylarsenous acid (GSAO) which has been radiolabelled with a radioisotope using a bifunctional chelator. In particularly preferred embodiments, the bifunctional chelator is 2,2'-(7-(1-carboxy-4-((2,5-dioxopyrrolidin-1-yl)oxy)-4-oxobutyl)-1,4,7-triazonane-1,4-diyl)diacetic acid (NODAGA), as shown in Formula (I) and Formula (Ia).

GSAO undergoes specific uptake into dead and dying cells. Without wishing to be bound by theory, it is thought that GSAO is retained in the cytosol of dying and dead cells via the formation of covalent bonds between the As(III) ion and the thiol groups of proximal cysteine residues. GSAO is a trivalent As (III) peptide, which has been found to activate the mitochondrial permeability transition pore. GSAO is toxic to proliferating cells and inhibits angiogenesis in vivo (Don A S, Kisker O, Dilda P et al (2003) *A peptide trivalent arsenical inhibits tumor angiogenesis by perturbing mitochondrial function in angiogenic endothelial cells. Cancer Cell* 3:497-509), but is nontoxic to quiescent endothelial cells in vitro. Conjugation of the γ-glutamyl residue of GSAO with fluorophores or radionuclides, as in the present invention, results in loss of its anti-angiogenic effect and gain in the ability to identify dying cells. When the plasma membrane integrity has been compromised the GSAO conjugate enters and binds to intra-cellular proteins, predominantly 90 kDa heat-shock proteins (Hsp90) (Park D, Don A S, Massamiri T et al (2011) *Non-invasive imaging of cell death using an Hsp90 ligand. J Am Chem Soc* 133:2832-2835); this protein is highly abundant in the cytosol, is only accessible when cell membrane integrity is compromised during cell death and is up-regulated in many malignancies (Hahn J S. *The Hsp90 chaperone machinery: from structure to drug development. BMB Rep.* 2009; 42(10):623-30). The As(III) motif of GSAO cross-links the unpaired thiols of Cys597 and Cys598 of Hsp90 forming a stable cyclic dithioarsinite.

Compounds according to the present disclosure labelled with radionuclide moieties are thus useful for imaging cell death in vitro and in vivo. In particular, radiolabelled conjugates as described herein can be used in diagnosing, treating and monitoring conditions associated with changes in cell death, for example neoplastic disorders or autoimmune disorders, for example tumours or for example cancer. Radiolabelled compounds of the present invention provide one or more advantages of being able to be readily synthesised for use in vivo using readily available and affordable materials, showing favourable biodistribution and imaging characteristics and radiation dosimetry, and being a non-invasive means of imaging and measuring cell death. Embodiments of the present disclosure enable imaging of treatment response earlier and in circumstances where it was previously not possible (such as very early after commencement of therapy), and would enable image guided personalised treatment, which is currently not possible as existing imaging modalities are insufficiently accurate or rapid.

Use of a radioisotope which has a half-life of less than 4 days in compounds of the present disclosure allows assessment of cell death to be undertaken on a practical and clinically relevant time scale. Z may be, for example, $^{11}$C, $^{64}$Cu, $^{13}$N, $^{15}$O, $\{Al^{18}F\}^{2+}$, $^{68}$Ga, $^{89}$Zr, $^{82}$Rb or $^{99m}$Tc. In preferred embodiments, Z has a half-life of less than 1 day, for example less than 12 hours, for example less than 8 hours, for example less than 6 hours, for example less than 4 hours, or for example less than 2 hours. In preferred embodiments, the compounds of the present disclosure are suitable for use in Positron Emission Tomography (PET). In particularly preferred embodiments, Z is $^{68}$Ga. $^{68}$Ga has a half-life of 68 minutes, meaning it is particularly useful for visualisation of cell death by way of PET; the use of such a short-lives positron emitting radioisotope allows imaging on a practical and clinically relevant timescale (i.e. long waits are not required following administration for images to be obtained). In addition, such a short half-life permits, in some instances, frequent serial and quantitative imaging. That is, repeated imaging may be conducted, allowing accurate changes in cell death over a time to be recorded, for example before and after administration of a chemotherapeutic agent or other treatment which induces cell death, such as radio-therapy, targeted therapy or immunotherapy or combinations thereof. Repeated measurements of the same subject allows more accurate assessment of cell death than single measurements made with reference to a standard value or image derived from a different subject. In contrast, the use of isotopes with much longer half-lives would require waits of multiple weeks between administration and imaging if any changes in cell death are to be visualised. In some alternative preferred embodiments, Z is $\{Al^{18}F\}^{2+}$. Such a radioisotope is particularly advantageous as $^{18}F$ is widely available, and has a half-life (109.7 minutes) which is both short enough to be particularly useful in Positron Emission Tomography, as described above, but also long enough to facilitate production and distribution of products containing the radioisotope without substantial decay.

In a particularly preferred embodiment, the compound according to Formula I is $^{68}$Ga-NODAGA-GSAO (i.e. the compound of Formula I wherein Z is $^{68}$Ga, $R_1$-$R_4$ are H, $R_5$ is —NHCH$_2$COOH, and A is As(OH)$_2$). Such an embodiment provides the above-mentioned advantages of being readily synthesised, being synthesised from readily available and affordable starting materials, exhibiting good biodistribution, low normal organ uptake, advantageous imaging characteristics, favourable radiation dosimetry, being non-invasive in use, and a short half-life suitable for sequential repeated imaging by Positron Emission Tomography and imaging on a clinically relevant and practical timescale.

According to a further aspect, the present disclosure also provides compounds according to Formula (Y)

Formula (Y)

wherein A is —As(OH)$_2$ or an arsenoxide equivalent group; each of $R_1$, $R_2$, $R_3$ and $R_4$ is independently selected from H, X, OH, NH$_2$, CO, SCN, —CH$_2$NH, —NHCOCH$_3$, —NHCOCH$_2$X or NO, and X is a halogen; $R_5$ is —NHCH$_2$COOH, OH or OR$_6$, wherein $R_6$ is a C$_{1-5}$ straight or branched alkyl group; and L is a bifunctional chelator; or a pharmaceutically acceptable salt, ester, prodrug or solvate thereof or derivative thereof.

In some preferred embodiments, the compound according to Formula (Y) is a compound according to Formula (Ya)

Formula (Ya)

The present disclosure provides a compound according to Formula (Y) which is a compound according to Formula II

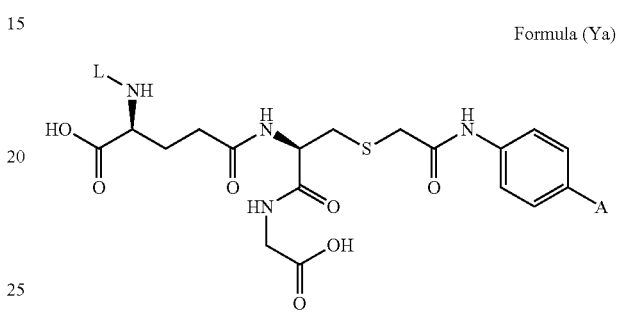

Formula (II)

wherein A is —As(OH)$_2$ or an arsenoxide equivalent group; each of $R_1$, $R_2$, $R_3$ and $R_4$ is independently selected from H, X, OH, NH$_2$, CO, SCN, —CH$_2$NH, —NHCOCH$_3$, —NHCOCH$_2$X or NO, and X is a halogen; $R_5$ is —NHCH$_2$COOH, OH or OR$_6$, wherein $R_6$ is a C$_{1-5}$ straight or branched alkyl group; or a pharmaceutically acceptable salt, ester, prodrug or solvate thereof.

Compounds of Formula (Y) are useful in the synthesis of Formula (X). In particular, compounds according to Formula (II) are useful in the synthesis of compounds according to Formula I, by radiolabelling of the NODAGA group. Such a synthesis is represented schematically below in Scheme 1, exemplified by NODAGA-GSAO as the starting material and $^{68}$Ga as the radioisotope.

Scheme 1
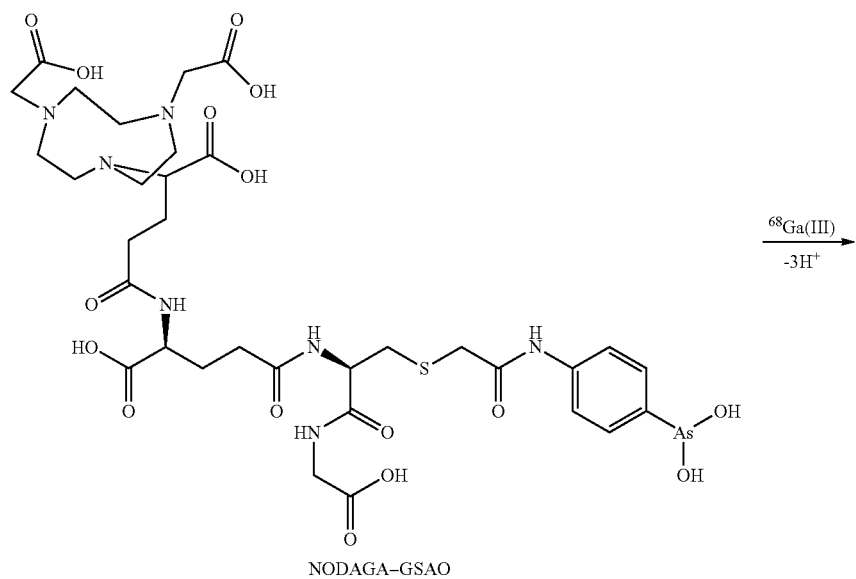
NODAGA–GSAO
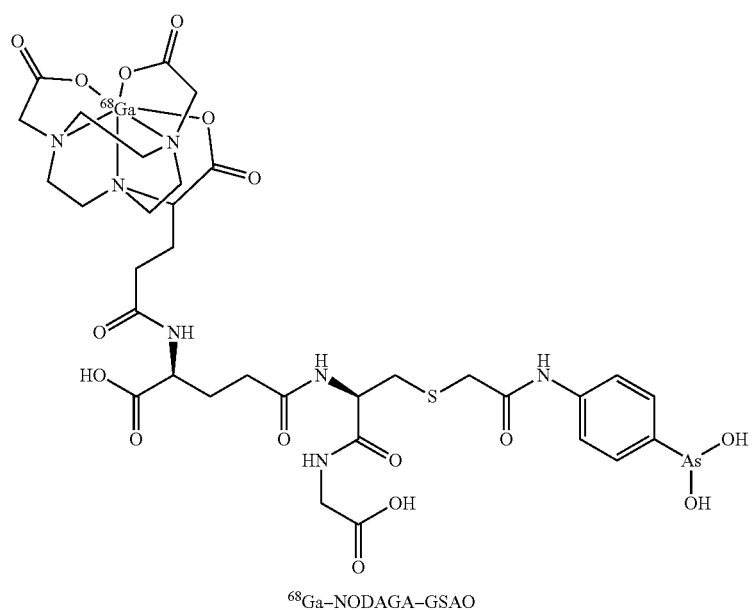
$^{68}$Ga–NODAGA–GSAO
In preferred embodiment, each of $R_1$, $R_2$, $R_3$ and $R_4$ are H. In further preferred embodiments, $R_5$ is —NHCH$_2$COOH.
In particularly preferred embodiments, the compound is a compound according to Formula (IIa)

Formula (IIa)

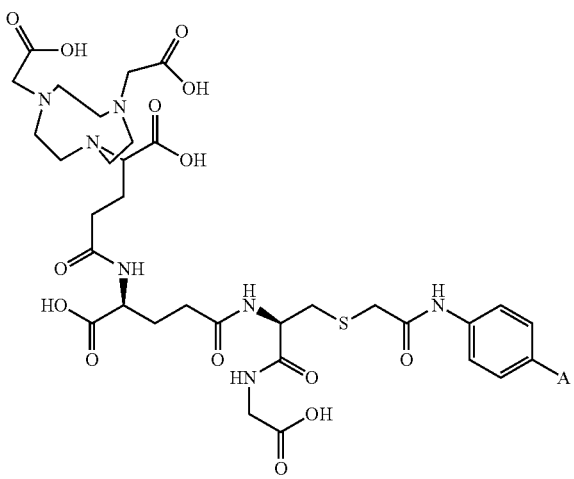

wherein A is as defined for Formula (II); or a pharmaceutically acceptable salt, ester, prodrug or solvate thereof.

In preferred embodiments, A is an arsenoxide group As(OH)$_2$.

In compounds suitable for use in the present invention, the arsenoxide group (—As(OH)$_2$) can typically be replaced by an arsenoxide equivalent.

The present disclosure provides a process for preparing a compound according to Formula (I) comprising mixing a radioisotope having a half-life of less than 4 days with a compound according to Formula (II), wherein the compound of Formula (I) or Formula (II) may be any of those described above In preferred embodiments, the mixing takes place at room temperature, i.e. without heating. The present disclosure provides a process for preparing a compound according to Formula (I) wherein Z is $^{68}$Ga, comprising eluting $^{68}$Ga onto a strong cation exchange column; and eluting the strong cation exchange column into a mixture comprising a compound according to Formula (II) and a buffer, wherein the buffer has a pH of about 4.5. In some embodiments, the mixing is carried out at room temperature, i.e. without heating. In some embodiments, the compounds according to Formula (I) and Formula (II) are compounds according to Formula (Ia) and Formula (IIa) respectively. The present disclosure further provides a process for preparing a compound according to Formula (X), comprising mixing a radioisotope having a half-life of less than 4 days with a compound according to Formula (Y), wherein the compound of Formula (X) or Formula (Y) may be any of those described above. In preferred embodiments, the mixing takes place at room temperature, i.e. without heating. The present disclosure provides a process for preparing a compound according to Formula (X) wherein Z is $^{68}$Ga, comprising eluting $^{68}$Ga onto a strong cation exchange column; and eluting the strong cation exchange column into a mixture comprising a compound according to Formula (Y) and a buffer, wherein the buffer has a pH of about 4.5. In some embodiments, the mixing is carried out at room temperature, i.e. without heating.

The present disclosure further provides pharmaceutical compositions and/or therapeutic formulations, that is, compounds of the present disclosure present together with a pharmaceutical acceptable carrier, excipient, diluent and/or vehicle.

For medical use, salts of the compounds according to the present disclosure may be used and they include pharmaceutically acceptable salts, although other salts may be used in the preparation of the compound or of the pharmaceutically acceptable salt thereof. By pharmaceutical acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio.

Pharmaceutically acceptable salts are well known in the art.

For instance, suitable pharmaceutically acceptable salts of the compounds of the present disclosure may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds of the present disclosure therefore include acid addition salts.

For example, S. M. Berge et al describe pharmaceutically acceptable salts in detail in *J. Pharmaceutical Sciences*, 1977, 66: 1-19. The salts can be prepared in situ during the final isolation and purification of the compounds of the present disclosure, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleat, malonate, methanesulfonate, 2-naphthalenesulfonate, nicotinate, nitrate, oleate, oxalate, palmitat, pamoate, pectinate, persulfate, 3-phenylpropionate, phosphate, picrate, pivalate, propionate, stearate, succinate, sulfate, tartrate, thiocyanate, toluenesulfonate, undecanoate, valerat salts, and the like. Representative alkali or alkaline earth metal salts include sodium, lithium potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The present disclosure also provides prodrugs. Typically, prodrugs will be functional derivatives of the compounds of the present disclosure which are readily converted in vivo to the required (active) compounds of the present disclosure, such as imaging, therapeutic and/or diagnostic agents.

Typical procedures for the selection and preparation of prodrugs are known to those of skill in the art and are described, for instance, in H. Bundgaard (Ed), *Design of Prodrugs*, Elsevier, 1985.

Intermediates and final products can be worked up and/or purified according to standard methods, e.g., using chromatographic methods, distribution methods, (re-)crystallization, and the like. The compounds, including their salts, may also be obtained in the form of solvates, in particular hydrates. In the context of the invention, solvates refer to those forms of the compounds according to the present disclosure which, in the solid or liquid state, form a complex by coordination with solvent molecules. Hydrates are a specific form of the solvates in which the coordination is with water. Crystals of the present compounds may, for example, include the solvent used for crystallization. Different crystalline forms may be present.

The present disclosure also relates to those forms of the process of preparing compounds according to the present disclosure in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

Single or multiple administrations of the compounds or pharmaceutical compositions can be carried out with dose levels and patterns being selected by the treating physician. Regardless, the compounds or pharmaceutical compositions of the present disclosure should provide a quantity of the compound sufficient to effectively treat or diagnose the patient, or visualise cell death in a subject.

One skilled in the art would be able, by routine experimentation, to determine an effective, non-toxic amount of the compounds or pharmaceutical compositions used in the invention which would be required to detect cells undergoing cell death and/or treat or prevent the disorders and diseases disclosed herein.

A compound of the present disclosure may be administered in a dose of, for example, up to 300 μg, for example up to 250 μg, for example up to 200 μg, for example up to 150 μg, for example up to 100 μg, for example up to 50 μg. In some embodiments, the compound of the present disclosure is administered in a dose of less than 50 μg, for example 10 to 50 μg.

Whilst the compounds of the present disclosure may be administered alone, it is generally preferable that the compound be administered as a pharmaceutical composition/formulation. In general pharmaceutical formulations of the compounds of the present disclosure may be prepared according to methods which are known to those of ordinary skill in the art and accordingly may include a pharmaceutically acceptable carrier, excipient, diluent, vehicle and/or adjuvant.

The carriers, excipients, diluents, vehicles and adjuvants must be "acceptable" in terms of being compatible with the other ingredients of the formulation, and not deleterious to the recipient thereof.

In some embodiments, pharmaceutical compositions of the present disclosure comprise a compound according to the present disclosure, as well as one or more further components selected from ascorbic acid, sodium, phosphate, acetate and chloride. In some embodiments, the pharmaceutical compositions comprises all such components. In a preferred form the pharmaceutical composition of a compound of the present disclosure comprises an effective amount of a compound according to the present disclosure, together with the pharmaceutically acceptable carriers, diluents and/or adjuvants as shown in Example 3.

The pharmaceutical compositions of the present disclosure may be administered by standard routes.

In particularly preferred embodiments, the compound or pharmaceutical composition of the present disclosure is administered intravenously. For administration as an injectable solution or suspension, non-toxic parenterally acceptable diluents or carriers can include, Ringer's solution, isotonic saline, phosphate buffered saline, ethanol and 1,2-propylene glycol.

The present disclosure provides compounds and compositions according to the present disclosure for use in detecting, imaging and/or visualising cell death. Such use may be in therapy, or in vivo diagnostics, or the use may be in an otherwise healthy subject. For example, the compounds according to the present disclosure may be used to visualise cell death in a subject by way of positron emission tomography (PET). When administered intravenously, the compounds of the present disclosure will target dying cells and may be visualised by virtue of their radiolabelling, thus providing information on the levels of cell death in different parts of a subject. The compounds according to the present disclosure may be used to provide a measure of cell death at a single point in time, i.e. by conducting a single PET scan. In some embodiments, more than one administration and/or scan may be carried out, before and after a stimulus is applied which induces cell death (for example a chemotherapeutic drug, radiotherapy, targeted therapy or immunotherapy, or a combination thereof), to assess the changes in levels of cell death before and after application of the stimulus.

Such visualisation of cell death may find use, for example, in assessing normal tissue toxicity of a substance, environmental condition or activity, for example an experimental therapy. Such compounds thus find use in research and drug development. The compounds may be used to assess cell death in drug screening in animal models of cancer and other conditions. The compounds may also be used to assess cell death in human tissues, for example during clinical trials, which is beneficial for patient safety, as well as potentially allowing more rapid dose escalation regimes by providing accurate feedback on the level of cell death given a particular dose. This would allow an individualised risk-adapted approach during trials, which is helpful in all patients, especially patients with altered renal or hepatic function or at the extremes of age. The compounds of the present disclosure find particular use in later phase oncology clinical trials, and are potentially useful for understanding overall and temporal treatment response, e.g. drug dosing and duration. For instance, in the event of a relatively modest overall response rate, use of the compounds may allow identification of a responding subpopulation to enable optimisation of future studies. Such use of the compounds may also help in demonstrating to regulatory authorities subpopulations with significant response to increase the likelihood of potential regulatory and reimbursement approval.

Provided herein are the compounds according to the present disclosure for use in therapy, and for use in in vivo diagnostics for example by PET imaging. Use in treatment and in vivo diagnosis may be for any condition associated with changes in levels of cell death, or conditions the treatment of which results in a change in levels of cell death. A change in cell death is a change (increase or decrease) relative to the level of cell death expected in the area in question in a healthy subject. For example, compounds of the present disclosure may be used in the diagnosis of a neoplastic condition, for example a tumour, for example a solid tumour and/or, for example, cancer. For example, a tumour may contain high levels of cell death and thus be visualised by use of the compounds of the present disclosure. Compounds of the present disclosure may further be used in the treatment of such conditions, by allowing visualisation of cell death and changes in the levels thereof in response to administration of a therapy, to determine whether or not treatment is successful. For example, successful treatment of neoplastic conditions, such as a tumour, or such as cancer following administration of a therapy intended to treat such condition can be determined by visualisation of increased levels of cell death at the site of the neoplastic condition by use of compounds of the present disclosure. Similarly, the compounds of the present disclosure may be used in the diagnosis or treatment of an autoimmune condition, wherein autoimmunity is causing cell death. Examples of autoimmune conditions include, but are not limited to, rheumatoid arthritis, systemic lupus erythematosus (SLE), multiple sclerosis, type 1 diabetes, Crohn's disease, vasculitis and seronegative arthropathies. The compounds according to the present disclosure may be used to diagnose and/or monitor the condition, and assess success of any treatments applied.

Even where a diagnosis has already been made and no therapy is applied, but a condition is associated with changes in levels of cell death, the compounds of the present disclosure find use in monitoring of the condition.

In treatment of conditions associated with cell death or the treatment of which causes a change in cell death, compounds of the present disclosure may be used to tailor or alter the treatment applied, for example the intensity, type or duration of treatment. The measure of cell death may indicate that a particular therapy is or is not proving effective; where it is ineffective, an alternative dose, or an alternative treatment may be adopted. Where it is effective, treatment may be continued if required, or reduced/discontinued if required. For example, compounds of the present disclosure may be used to visualise cell death in response to an applied treatment, and the treatment dose adjusted accordingly dependent on the level of cell death. For example, identification of patients in whom there is little or no tumour cell death following therapy would indicate the need for either an increase in the dose or duration of current treatment (escalation) or a change to more intensive or multimodal therapies in order to maximise the chance of cure or disease control. Conversely, accurately assessing response early on in the course of treatment would allow a reduction in either the duration or intensity of treatment in cancer patients who are responding well in order to avoid treatment related morbidity and mortality (de-escalation) without compromising the chance of cure or disease control. An assessment of cell death may cause the adoption of a new therapy, where the measure of cell death following an initial therapeutic approach suggests that the initial approach is not successful.

The present disclosure further provides methods of treating or diagnosing the above-mentioned conditions, or of visualising cell death, or of monitoring such conditions by administration of a compound described herein. The present disclosure further provides use of the compounds described herein in such methods, and use in the manufacture of medicaments for the treatment of such conditions. Use of the compounds described herein as imaging agents, for example in PET, and to visualise cell death is also provided herein.

Use of the compounds of the present disclosure and methods of treatment or diagnosis provided herein, for example of the conditions described above, include administration of an effective amount of a compound described herein to a subject. The method may further comprise conducting PET on the subject following administration of the compound described herein, for example immediately after administration of the compound described herein. In alternative embodiments, any suitable imaging method other than PET may be used to image the compound described herein.

In some embodiments, PET scans are carried out after a time interval of at least 10 minutes, for example at least 20 minutes, at least 30 minutes, at least 40 minutes, at least 50 minutes, or at least 1 hour following administration of the compound according to the present disclosure. In some embodiments, multiple PET scans may be carried out at various times following administration. For example, the compound of the present disclosure may be administered, and a PET scan may be carried out immediately following administration, as well as at about 30 minutes, about 1 hour, about 2 hours and about 3 hours following administration.

In some embodiments, the method of diagnosis or treatment comprises administration of a species which induces cell death, for example a chemotherapeutic agent, radiotherapy, targeted therapy or immunotherapy, or a combination thereof, in the treatment of a tumour, wherein the compound of the present disclosure may be administered to visualise the effectiveness of the species in inducing cell death. For example, a chemotherapeutic agent, radiotherapy, targeted therapy or immunotherapy or combination thereof may be administered to a subject together with, prior to or subsequent to administering a compound of the present disclosure. PET scans may be carried out following administration of the compound to visualise the cell death-inducing activity of the chemotherapy, radiotherapy, targeted therapy or immunotherapy, or combination thereof.

In some embodiments, an administered species, for example a drug, may have the effect of reducing cell death, and as such a visualisation of cell death following administration of such a species may show reduced cell death in the target area.

Some administered species, for example a drug, may take some time before its effects are shown; visualisation of cell death, such as by a PET scan, may therefore take place a longer time after administration of the species, for example 1 day, 3 days, 5 days, 1 week, 2 weeks or a month following administration; in such cases, a compound according to the present disclosure may be administered prior to the scan, in addition to or instead of prior to administration of the drug or other species.

In some particular embodiments, the present disclosure provides a method of assessing a response of a subject to a therapy intended to cause a change in level of cell death, comprising: administering the therapy; administering a compound according to the present disclosure; and visualising cell death. In one particular embodiment, the cell death is visualised by conducting positron emission tomography on the subject. In one particular embodiment, the therapy intended to cause a change in level of cell death is chemotherapy, radiotherapy, targeted therapy or immunotherapy, or a combination thereof. In therapies intended to cause an increase in the level of cell death in a particular part of a subject, such as chemotherapy, radiotherapy, targeted therapy or immunotherapy, or a combination thereof, the assessment will show success of the therapy when a high level of cell death is visualised in the desired location. In some embodiments, a compound according to the present disclosure is administered and/or cell death is also visualised prior to administration of the therapy, to allow comparison between the level of cell death before and after administration of the therapy. In such instances, an increase in the level of cell death between the two visualisations may indicate successful therapy. Conversely, low levels of cell death or a decrease in cell death may indicate unsuccessful or sub-optimal therapy. In some alternative embodiments, a therapy is intended to decrease the level of cell death in a particular part of a subject; in such embodiments, a low level of cell death or decreased level of cell death in the area of interest indicates successful therapy, and a high level of cell death or increased cell death indicates unsuccessful or sub-optimal therapy.

In the above methods, administration of the compound of the present disclosure and visualisation of cell death may take place, for example, about 1 day, about 2 days, about 3 days, about 1 week, about 2 weeks, about 3 weeks, about 4 weeks, about 5 weeks and/or about 6 weeks following administration of the therapy. In some embodiments, administration of the compound of the present disclosure and visualisation of cell death takes place within 7 days of administration of the therapy. In some embodiments, administration of the compound of the present disclosure and visualisation of cell death takes place at least 4 weeks following administration of the therapy. In some embodiments, administration of the compound of the present disclosure and visualisation of cell death takes place more than once following administration of the therapy. For example, in some embodiments, administration of the compound of the present disclosure and visualisation of cell death takes place both within 7 days of and at least 4 weeks following administration of the therapy.

In the above methods, visualisation of cell death, for example by positron emission tomography, may take place, for example, at least 10 minutes, at least 20 minutes, at least 30 minutes, at least 40 minutes, at least 50 minutes, at least 1 hour or at least 90 minutes following administration of the compound according to the present disclosure. For example, the compound of the present disclosure may be administered, and visualisation may be carried out, for example, immediately following administration, or about 30 minutes, about 1 hour, about 90 minutes, about 2 hours or about 3 hours following administration of the compound according to the present disclosure.

The present disclosure relates to the above methods, compounds according to the present disclosure for use in such methods, use of compounds of the present disclosure in such methods, and use of compounds according to the present disclosure in the manufacture of a medicament for use in such methods.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The reference in this specification to any prior publication (or information derived from it), or to any matter which is known, is not, and should not be taken as, an acknowledgement or admission or any form of suggestion that prior publication (or information derived from it) or known matter forms part of the common general knowledge in the field of endeavour to which this specification relates.

The present disclosure will now be described with reference to the following specific examples, which should not be construed as in any way limiting the scope of the invention.

EXAMPLES

Example 1

Synthesis of NODAGA-GSAO a) GSAO was prepared using the process described in Park D, Don A S, Massamiri T et al (2011) *Non-invasive imaging of cell death using an Hsp90 ligand. J Am Chem Soc* 133:2932-3835; 4-(N-(bromoacetyl)amino)phenylarsonic acid (BRAA) was synthesized from p-arsanilic acid and bromoacetyl bromide, and BRAA reduced to 4-(N-(bromoacetyl)amino) phenylarsonous acid (BRAO). BRAO was coupled to glutathione (GSH) to produce GSAO. The GSAO was resolved from unreacted BRAO and GSH by C18 chromatography.

b) Sodium bicarbonate and ultrapure water were purged with nitrogen for 30 minutes prior to use. The reaction setup and purification were performed under an inert atmosphere of nitrogen. GSAO obtained from step a) (20.0 mg, 36.5 µmol) was dissolved in 0.1 N sodium bicarbonate (7.4 mL) at 4° C. and stirred for 10 minutes.

c) NODAGA-NHS (2,2'-(7-(1-carboxy-4-((2,5-dioxopyrrolidin-1-yl)oxy)-4-oxobutyl)-1,4,7-triazonane-1,4-diyl)diacetic acid mono-N-hydroxysuccinimide ester) obtained from CheMatech (Dijon, France) (34.5 mg, 47.0 µmol) was dissolved in anhydrous dimethylformamide (DMF) (1 mL) and added to the reaction mixture obtained in step b) dropwise over 1 hour.

d) The reaction mixture was stirred for 4 hours, acidified by the addition of 1 M hydrochloric acid (1 mL), shock-frozen in liquid nitrogen, and freeze-dried.

NODAGA-GSAO Purification e) The residue resulting from step d) was redissolved in deaerated water (4 mL), filtered (0.45 µm), and purified by reverse phase high-performance liquid chromatography (RP-HPLC). A gradient of 2-20% mobile phase B (0.2% trifluoroacetic acid (TFA) in acetonitrile) in mobile phase A (0.2% TFA in ultrapure water) was applied from 0 to 25 minutes. NODAGA-GSAO was eluted at 20.6 minutes. The sample was collected by hand and each fraction was instantly purged with nitrogen.

HPLC was carried out on a Shimadzu LC-20 series LC system with two LC-20AP pumps, a SIL-10AP autosampler, an SPD-20A UV/VIS detector, and a Shimadzu ShimPack GIS-C18 column (150×10.0 mm i.d., 5 µm, 4 mL/mini) (System A). Shimadzu LabSolutions Software (Ver. 5.73) was used for data acquisition and processing.

f) The pooled fractions were frozen at −20° C. and freeze-dried to give 7.3 mg of white powder (21.6% yield).

g) NODAGA-GSAO was dispensed in aliquots of 54 µg per 100 µL water and stored at −20° C.

h) The purity of the compound (>95%) was verified by injecting a solution of NODAGA-GSAO (5 µL; approx. 17 mM, in water) onto liquid chromatography-mass spectrometry (LC-MS) at 2-2-50% mobile phase B (0.1% formic acid (FA) in acetonitrile) in mobile phase A (0.1% FA in mass spectrometry-grade water) over 0-5-45 minutes. NODAGA-GSAO eluted at 19.4 minutes.

LC-MS was conducted using an Agilent system (Santa Clara, CA, USA) consisting of a 1260 series quaternary pump with an inbuilt degasser, 1200 series autosampler, thermostated column compartment, diode array detector, fraction collector, a 6120 series single-quadrupole mass spectrometer, and an Agilent Zorbax Eclipse XDB-C18 column (150×4.6 mm i.d., 5 µm) at 30° C. (System B). The drying gas flow, temperature, and nebulizer were set to 12 L/min, 350° C., and 35 psi respectively. Agilent OpenLAB Chromatography Data System (CDS) ChemStationEdition (C.01.05) was used for data acquisition and processing. Electrospray ionization (ESI) was used to analyse aliquots (5 µL) in positive ion mode with a 3500 V capillary voltage. Nuclear magnetic resonance (NMR) spectroscopy ($^1$H and $^{13}$C) spectra were recorded in 5 mm Pyrex tubes (Wilmad, USA) using a Varian 400-MR NMR spectrometer (Lexington, MA, USA) at a frequency of 399.73 MHz ($^1$H) or 100.51 MHz ($^{13}$C) at 24° C. operated with VnmrJ 3.1 software (Agilent Technologies, Santa Clara, CA, USA).

The spectral data are reported in ppm (δ) and referenced to residual solvent (deuterated dimethyl sulfoxide [DMSO-$d_6$] 2.50/39.52 ppm).

i) Absorbance was measured at 210 and 254 nm and the respective area under the curve (AUC) was used to determine compound purity as a percent of total AUC compared to background.

Example 2

Figure 2:
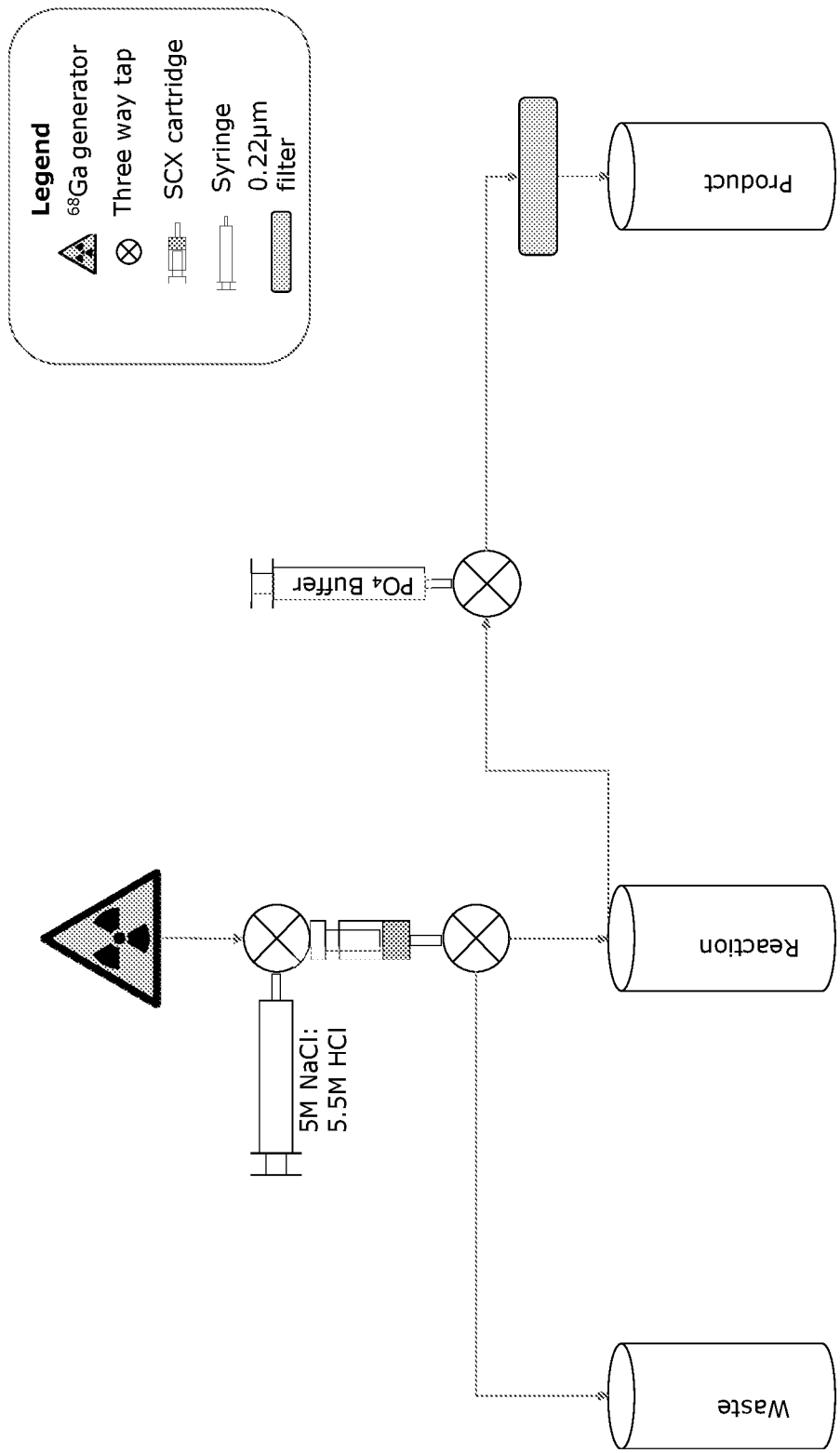
FIG. 2 is a schematic diagram of a $^{68}$Ga-NODAGA-GSAO radiolabelling system as used in Example 2.

Radiolabelling of NODAGA-GSAO with $^{68}$Ga a) The barrel of the BondElute SCX column was cut so that when inserted the barbed female luer thread rested just above the column media to create a cartridge (hereafter referred to as the SCX cartridge). The barbed female luer thread should be fitted firmly and securely into the cut barrel of the BondElute SCX column to create a sealed cartridge that is air- and liquid-tight.

b) The SCX cartridge was primed with 1 mL 5.5 M HCl and then flushed with 10 mL of water.

c) The SCX cartridge was purged with air.

d) Ascorbic acid solution (0.25 M) was obtained by dissolving 44 mg of ascorbic acid in 1 mL water (Water Ultrapur, Merck).

e) A sodium acetate buffer (1.5 M $CH_3COON\cdot 3H_2O$, pH4.5) was obtained by dissolving 10.21 g $CH_3COONa\cdot 3H_2O$ in water (Water Ultrapur, Merck). The pH was adjusted to pH 4.5 with glacial acetic acid and water was added to a total volume of 50 mL f) One vial of 54 μg NODAGA-GSAO obtained in Example 1 was thawed and mixed with 100 μL of ascorbic acid solution (used as a free radical scavenger since GSAO is sensitive to radiolysis and oxidation), 250 μL of sodium acetate buffer, and 3.5 mL water and the mixture transferred to a 10 mL evacuated glass reaction vial.

g) The $^{68}$Ge/$^{68}$Ga was eluted according to the supplier's instructions onto the primed SCX cartridge.

h) The SCX cartridge was purged with air.

i) The contents of the SCX cartridge were eluted into the reaction vial with 500 μL of the NaCl/HCl elution mixture followed by 0.5 mL air, using B. Braun Sterican needles to minimize leaching of metal ions from the needles. The contents of the reaction vial were briefly mixed and allowed to react at room temperature for 10 minutes.

j) 3 mL of phosphate buffer was added to the reaction vial. The contents of the reaction vial were withdrawn with a 10 mL syringe and passed through a 0.22 μm filter into a new sterile vial yielding the final product for injection. No post-purification of the product was performed as $^{68}$Ga-NODAGA-GSAO was not significantly retained on C-18 cartridges and a suitable biocompatible post-purification cartridge/solvent system has not been identified. Despite this, the method described produced $^{68}$Ga-NODAGA-GSAO of high radiochemical purity and specific activity, exceeding current release requirements for $^{68}$Ga radiopharmaceuticals.

k) A sterile, closed radiolabelling system is used for the above procedure, as is preferred for preparation for human use and also for minimization of the risk of radioactive contamination to the operator and environment (FIG. 2). This may also be automated using a radiochemistry synthesis module.

Figure 3:
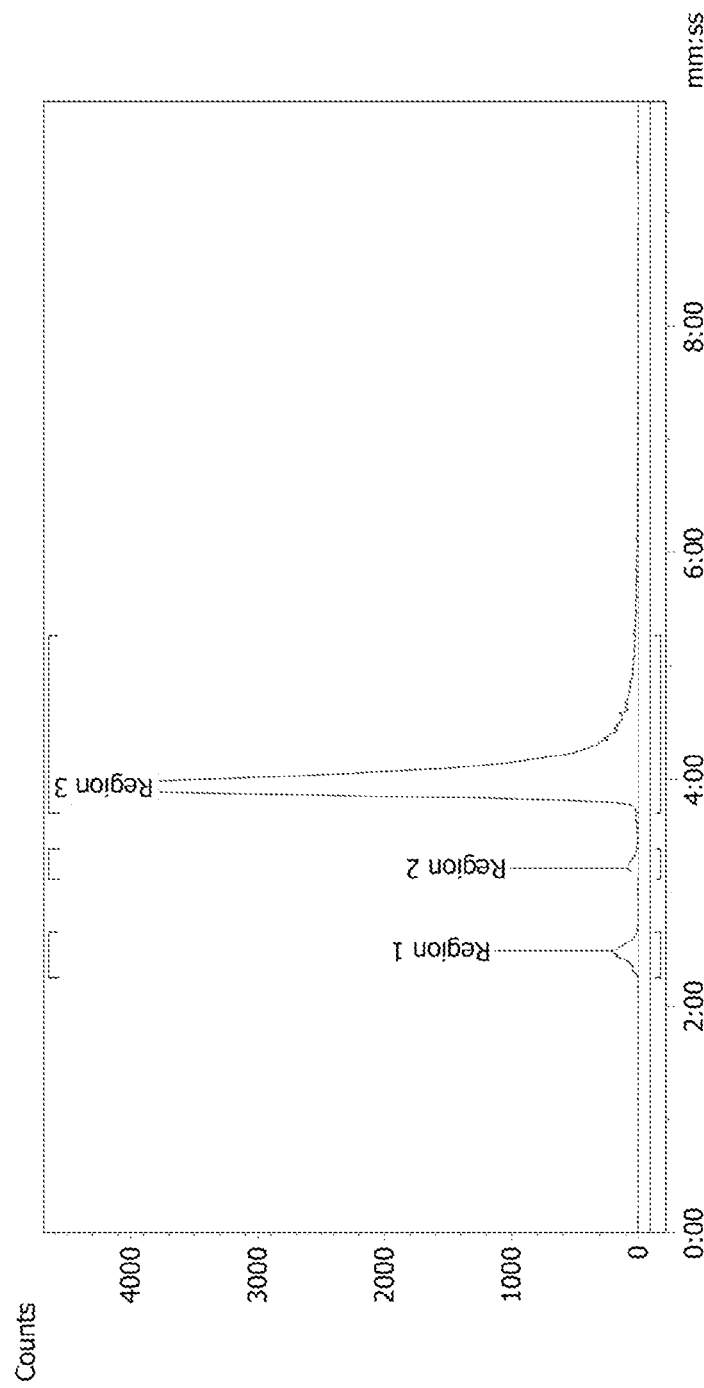
FIG. 3 is a radiometric HPLC chromatogram of the final product produced in Example 2.
Figure 4:
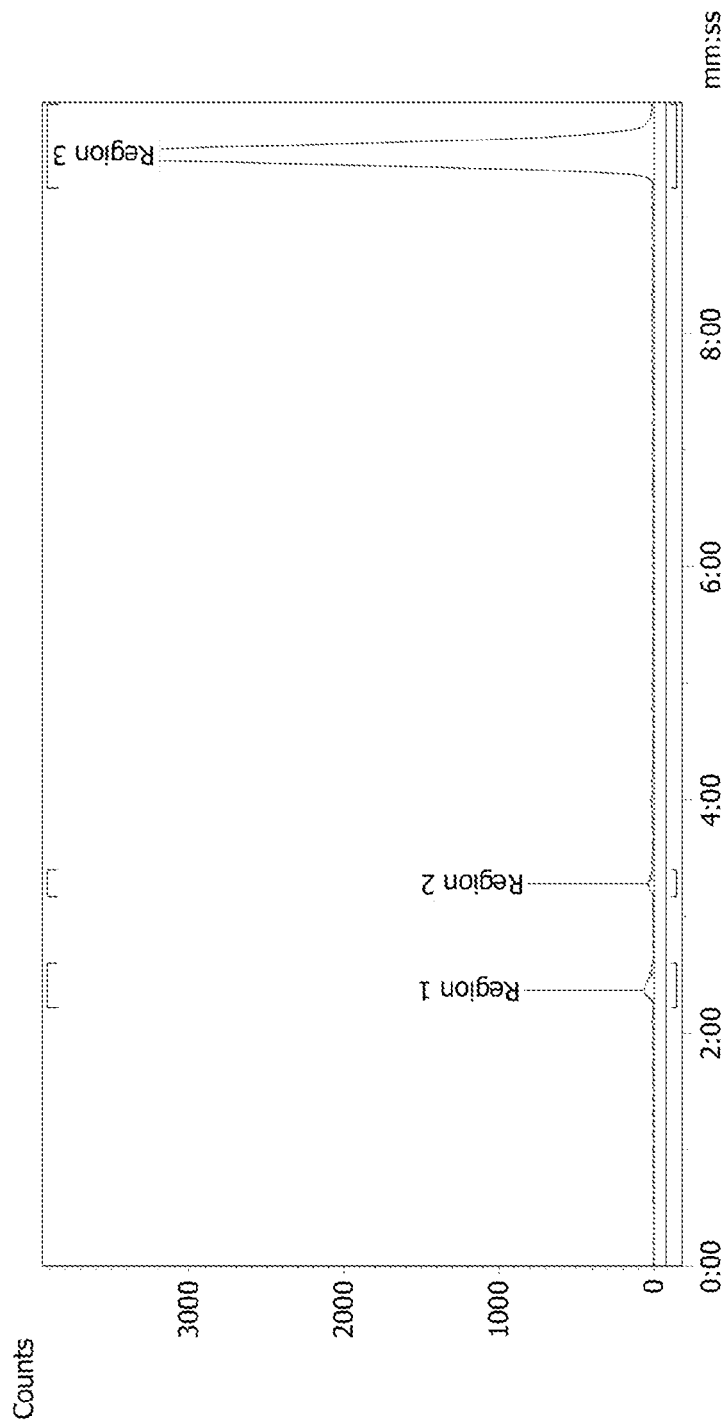
FIG. 4 is a radiometric HPLC chromatogram of the final product produced in Example 2 (the same product as FIG. 4) following reaction with 2,3-Dimercapto-1-propanol (DMP).

Purity of $^{68}$Ga-NODAGA-GSAO l) Radiochemical purity of $^{68}$Ga-NODAGA-GSAO (approximately 100 μL sample of the final product obtained in step h) above) was assessed by HPLC system C at 9-9-60% mobile phase B (acetonitrile) in mobile phase A (0.1% TFA in ultrapure water) over 0-6-10 minutes using radiometric detection. The AUC of $^{68}$Ga-NODAGA-GSAO peak over the sum of all radiometric peaks greater than three times background was used to determine radiochemical purity. Absorbance was also measured at 210 and 280 nm; however, the molar quantities were below the limits of reliable absorbance detection and were therefore not used for assessment of purity. $^{68}$Ga-NODAGA-GSAO was eluted with a retention time of approximately 3 minutes and 55 seconds, as shown in the radiometric HPLC chromatogram of the final product in FIG. 3: region 1 is corresponds to $^{68}$Ga, region 2 corresponds to oxidation products, and region 3 corresponds to $^{68}$Ga-NODAGA-GSAO. The release criterion used for radiochemical purity of $^{68}$Ga-NODAGA-GSAO in the final product was ≥91% (*European Pharmacopeia* (2016) 01/2013:2482 *Gallium (68Ga) Edotreotide injection correct* 8.6. *European Pharmacopeia*, 9$^{th}$ edn, pp 1150-1152).

m) Further assessment of the radiochemical purity of $^{68}$Ga-NODAGA-GSAO was performed by reacting 200 μL of the final product with 5 μL of DMP/DMSO solution at room temperature with occasional agitation for 10 minutes. Approximately 100 μL of this mixture was assessed by HPLC system C at 9-9-60% mobile phase B (acetonitrile) in mobile phase A (0.1% TFA in ultrapure water) over 0-6-10 minutes using radiometric detection. The DMP-$^{68}$Ga-NODAGA-GSAO peak (with a retention time of approximately 9 minutes and 30 seconds) over the sum of all radiometric peaks greater than three times background should be ≥91%; as DMP binds with very high affinity to the phenylarsonous moiety of $^{68}$Ga-NODAGA-GSAO this will abolish the usual $^{68}$Ga-NODAGA-GSAO peak with a retention time of approximately 3 minutes and 55 seconds and result in a new peak with a retention time of approximately 9 minutes and 30 seconds. This provides specific information about the radiochemical purity of the active GSAO and is able to distinguish between $^{68}$Ga-NODAGA-GSAO and other products, such as oxidized degradation products of GSAO. However, this is not included in the required release criteria to minimise loss of product due to decay. The Radiometric HPLC chromatogram obtained is shown in FIG. 4: region 1 corresponds to unchelated $^{68}$Ga, region 2 corresponds to oxidation products, and region 3 corresponds to DMP-$^{68}$Ga-NODAGA-GSAO.

n) Assessment of colloidal contaminants was performed by instant thin-layer chromatography developed in 0.9% NaCl. Colloidal contaminants remained at the origin while $^{68}$Ga-NODAGA-GSAO had Rf>0.5. The release criterion used for colloid contaminants with total radioactivity with Rf≥0.5 was ≥90%.

o) Half-life was determined by a minimum of four measurements over 10 minutes performed on a dose calibrator. The release criterion used was a calculated half-life between 64 and 72 minutes (the half-life determination is required to confirm the absence of significant $^{68}$Ge breakthrough).

Sterility and Pyrogenicity Testing p) Sterility and pyrogenicity were initially tested in an appropriately accredited laboratory on three serial syntheses to confirm that for the process sterility and pyrogenicity are within pharmacopoeia guidelines (*European Pharmacopeia* (2016) 01/2013:2482 *Gallium $^{68}$Ga Edotreotide injection correct* 8.6. *European Pharmacopeia*, 9$^{th}$ edn, pp 1150-1152). Subsequent random testing of preparations is performed at regular intervals.

Example 3

Pharmaceutical Formulation of $^{68}$Ga-NODAGA-GSAO

A composition was prepared containing ingredients in the amounts listed in Table 1 below.

TABLE 1

| Ingredient Name | Quantity | Unit |
|---|---|---|
| Ascorbic acid | 4.4 | mg |
| Sodium | 95 | mg |
| Phosphate | 109 | mg |
| Acetate | 22 | mg |
| Chloride | 91 | mg |
| $^{68}$Ga-NODAGA-GSAO | 200 | MBq |

Example 4

Biodistribution of $^{68}$Ga-NODAGA-GSAO

Biodistribution was studied in ten healthy male rats (Lewis, Liverpool Hospital Animal Facility) aged 6-8 weeks. Five rats were administered with $^{68}$Ga-NODAGA-GSAO. The rats were housed singly in a cage with impervious absorbent matting and at 1 hour post administration 5 rats were sacrificed by lethal carbon dioxide overdose. Immediately post mortem, blood was sampled via cardiac puncture. Two of the 5 rats were then imaged by PET CT (GE Discovery 710). The PET CT scan comprised a CT scan (80 kVp, 20 mA, helical mode, reconstructed slice thickness of 0.625 mm) followed by a PET scan (2 bed positions, 7.5 min/bed position, 256×256 reconstruction matrix, slice thickness 3.27 mm).

All of the rats were then dissected, organs sampled and weighed and counted in a gamma counter, and the cpm value converted to MBq using a known standard. The activity in the remaining carcass was measured in a dose calibrator.

Biodistribution studies were performed in a further 5 rats at two hours following 68Ga-NODAGA GSAO administration.

Injected activity was corrected by measuring residual activity left in the syringe after injection in a dose calibrator. To correct for any dose extravasated at the injection site the tail was harvested and the activity in the tail was subtracted from the administered activity. All calculations were decayed corrected using the injection time as the reference.

Biodistribution was expressed as % ID/g and % ID/organ. % retained activity was the sum total of all activity in all individually harvested organs as well as the activity in the remaining carcass as a percentage of the injected dose. % recovered activity was the sum total of all activity in all individually harvested organs as well as the activity in the remaining carcass and excreted activity in the impervious matting as a percentage of the injected dose.

Results

The rats weighed an average of 170 g (range 120-229 g, standard deviation 32.2 g). The average injected activity was 27.3 MBq (range 18.9-38.6 MBq, standard deviation 7.4 MBq).

For the 1 hour biodistribution group, the mean uptake time was 62.6 (range 60-65) minutes and for the 2 hour biodistribution group the mean uptake time was 122.2 (range 120-126) minutes.

Figure 5:
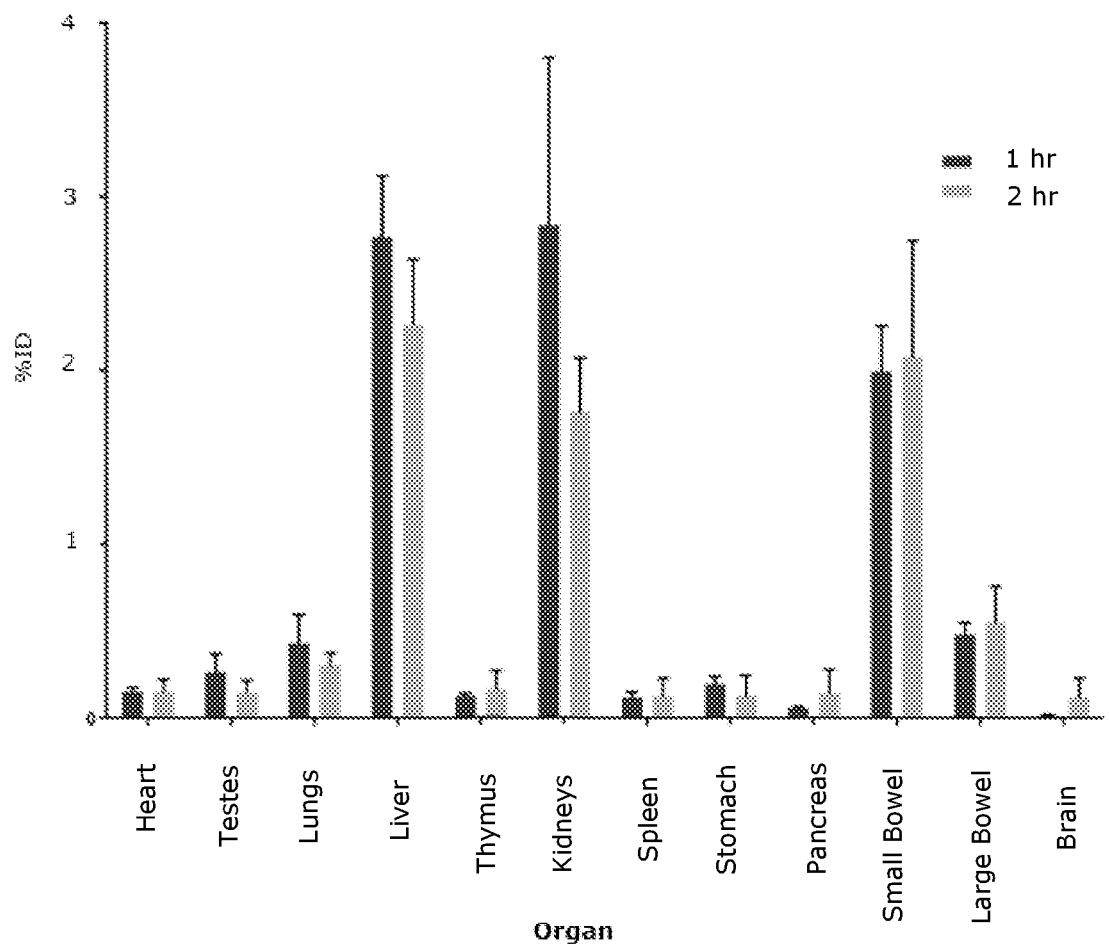
FIG. 5 shows the biodistribution of $^{68}$Ga-NODAGA-GSAO (% ID/g) in healthy male rats at 1 and 2 hours post administration of $^{68}$Ga-NODAGA-GSAO.

FIG. 5 shows the organ biodistribution of $^{68}$Ga-NODAGA-GSAO (% ID/g) in healthy male rats at 1 and 2 hours post administration of $^{68}$Ga-NODAGA-GSAO.

As seen in FIG. 5, the highest concentration of $^{68}$Ga-NODAGA-GSAO is in the kidneys, and the organs with the greatest uptake of $^{68}$Ga-NODAGA-GSAO are the kidneys, liver and small bowel. The high renal and hepatic uptake is consistent with renal excretion and hepatic metabolism while the small bowel uptake is likely to reflect uptake within dead and dying small bowel epithelial cells.

At 1 hour 32.4% (range 24.9-38.2%, SD 5.6%) of injected activity was retained and at 2 hours 21.4% (range 11.2-32.1%, SD 7.5%) of injected activity was retained within the animal. Overall mean total recovered activity at 1 hour was 84.9% (range 55.3-107.9%, SD 19.0%) and at 2 hours total recovered activity was 75.3% (range 50.0-120.9%, SD 27.2%) of injected activity.

Imaging

Figure 6:
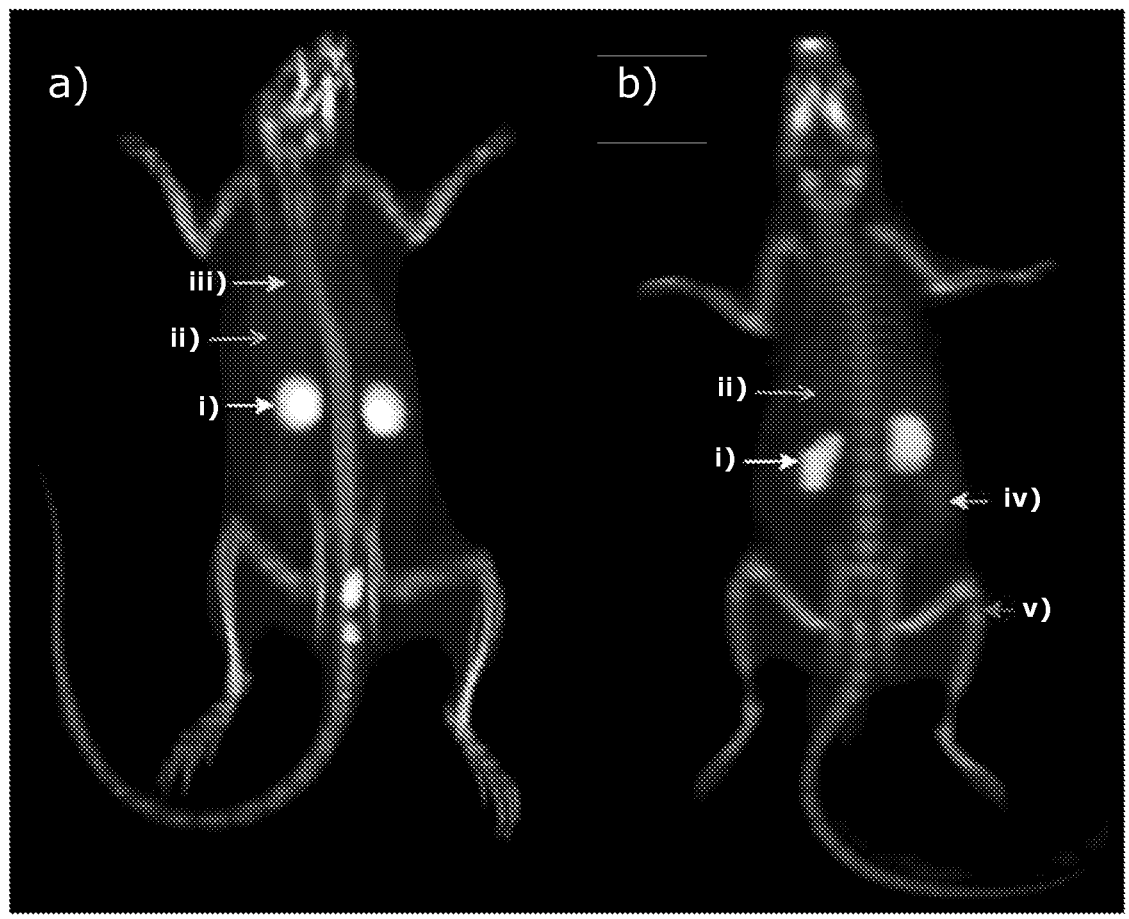
FIG. 6 shows the maximum intensity projection of $^{68}$Ga-NODAGA-GSAO PET CT scans performed a) 1 hour and b) 2 hours following tracer ($^{68}$Ga-NODAGA-GSAO) administration.

PET CT images demonstrated findings concordant with the quantitative biodistribution data. FIG. 6 shows the maximum intensity projections of $^{68}$Ga-NODAGA-GSAO PET CT scans performed a) 1 hour and b) 2 hours following tracer ($^{68}$Ga-NODAGA-GSAO) administration.

The images performed one hour after tracer administration demonstrate a high concentration of tracer in the kidneys (arrows i) in FIGS. 6 a) and b)), with lower levels of uptake in the liver (arrows ii)). There is residual blood pool activity in the mediastinum (arrow iii)) similar to that of the liver. In the images performed 2 hours after administration (FIG. 6b) there is again a high concentration of tracer in the kidneys with lower levels of uptake in the liver. There is no longer visible blood pool activity in the mediastinum. In both the sets of images there is uptake in the small bowel (arrow iv)) and in the physes (arrow v)) likely due to specific uptake at sites of high physiological cell death.

Example 5

Radiation Dosimetry

The biodistribution data derived above was used to estimate human radiation dosimetry using the methods described by Stabin for a standard adult male (Stabin and Siegel 2003). The % ID/g for a given standard male organ was extrapolated from the rat biodistribution data using the following equation:

$$\left(\frac{\% \, ID}{\text{Organ}}\right)_{human} = \left[\left(\frac{\% \, ID}{g_{organ}}\right) \times (g_{TBweight})_{animal}\right] \times \left(\frac{g_{organ}}{g_{TBweight}}\right)_{human}$$

Mono-exponential clearance curves for each organ and total remaining tissues were fitted using tools in OLINDA/EXM software. Given the rapid excretion of $^{68}$Ga-NODAGA-GSAO it was assumed that all excretion was via urine (i.e. urinary half clearance time was calculated using a mono-exponential fit and was assumed to be 1–% total retained activity at each time point). For the voiding bladder model it was assumed that patients would void 1 hour following administration.

Whole body effective dose was estimated at 2.13E-02 mSv/MBq. Assuming an injected activity of 150 MBq this results in a whole body effective dose of 3.2 mSv, a dose lower than from a diagnostic CT scan of the abdomen and lower than FDG-PET CT. Estimated human individual organ doses are listed in Table 2 below (ULI=upper large intestine, LLI=lower large intestine).

TABLE 2

| Target Organ | Alpha | Beta | Photon | Total | ED Cont. |
|---|---|---|---|---|---|
| Adrenals | 0.00E000 | 2.13E-03 | 1.89E-03 | 4.02E-03 | 2.01E-05 |
| Brain | 0.00E000 | 8.15E-04 | 5.73E-04 | 1.39E-03 | 6.94E-06 |
| Breasts | 00.00E000 | 2.13E-03 | 8.94E-04 | 3.02E-03 | 1.51E-04 |
| Gallbladder Wall | 0.00E000 | 2.13E-03 | 2.15E-03 | 4.28E-03 | 0.00E000 |
| LLI Wall | 0.00E000 | 2.13E-03 | 5.09E-03 | 7.23E-03 | 8.67E-04 |
| Small Intestine | 0.00E000 | 5.18E-03 | 3.03E-03 | 8.21E-03 | 4.10E-05 |
| Stomach Wall | 0.00E000 | 2.61E-03 | 1.61E-03 | 4.22E-03 | 5.06E-04 |
| ULI Wall | 0.00E000 | 2.53E-03 | 2.63E-03 | 5.16E-03 | 2.58E-05 |
| Heart Wall | 0.00E000 | 3.09E-03 | 1.55E-03 | 4.65E-03 | 0.00E000 |
| Kidneys | 0.00E000 | 2.27E-02 | 3.56E-03 | 2.62E-02 | 1.31E-04 |
| Liver | 0.00E000 | 4.76E-03 | 2.04E-03 | 6.80E-03 | 3.40E-04 |
| Lungs | 0.00E000 | 5.42E-03 | 1.38E-03 | 6.80E-03 | 8.16E-04 |
| Muscle | 0.00E000 | 2.13E-03 | 2.04E-03 | 4.18E-03 | 2.09E-05 |
| Ovaries | 0.00E000 | 2.13E-03 | 4.89E-03 | 7.02E-03 | 1.40E-03 |
| Pancreas | 0.00E000 | 3.87E-03 | 2.03E-03 | 5.90E-03 | 2.95E-05 |
| Red Marrow | 0.00E000 | 1.49E-03 | 1.89E-03 | 3.38E-03 | 4.05E-04 |
| Osteogenic Cells | 0.00E000 | 3.31E-03 | 1.67E-03 | 4.98E-03 | 4.98E-05 |
| Skin | 0.00E000 | 2.13E-03 | 1.06E-03 | 3.19E-03 | 3.19E-05 |
| Spleen | 0.00E000 | 4.05E-03 | 1.86E-03 | 5.91E-03 | 2.95E-05 |
| Testes | 0.00E000 | 2.21E-03 | 3.49E-03 | 5.69E-03 | 0.00E000 |
| Thymus | 0.00E000 | 4.48E-03 | 1.36E-03 | 5.84E-03 | 2.92E-05 |
| Thyroid | 0.00E000 | 2.13E-03 | 1.15E-03 | 3.28E-03 | 1.64E-04 |
| Urinary Bladder Wall | 0.00E000 | 2.84E-01 | 3.92E-02 | 3.24E-01 | 1.62E-02 |
| Uterus | 0.00E000 | 2.13E-03 | 9.42E-03 | 1.15E-02 | 5.77E-05 |
| Total Body | 0.00E000 | 2.68E-03 | 1.93E-03 | 4.61E-03 | 0.00E000 |

Discussion

As shown in the above-described experiments, $^{68}$Ga-NODAGA-GSAO has advantageous imaging characteristics, with relatively little interference from physiologic renal and hepatic activity. In addition, the rapid clearance suggests that imaging between 1 and 2 hours post injection is feasible and thus well suited to using $^{68}$Ga (clinically for $^{68}$Ga-based somatostatin receptor expression imaging, imaging is performed at 45-90 minutes following injection). Of note from the $^{68}$Ga-NODAGA-GSAO PET/CT images (FIG. 6) is the visualisation of uptake within small and large bowel and also in the physes of the long bones, which may represent uptake in areas of high rates of physiologic cell death. The imaging appearances are confirmed by the measured distribution, and in contrast to some other organs (especially the liver and kidneys) uptake is higher at the 2 hour time point then at one hour post-injection, suggesting that the uptake in bowel may represent specific binding rather than non-specific tracer diffusion.

The estimated human radiation dosimetry is favourable, with an estimated total body effective dose of 0.021 mSv/MBq which, assuming a standard injected dose of 150 MBq, would deliver a total dose whole body effective dose of 3.2 mSv. The dose limiting organ is the urinary bladder wall with a dose of 0.32 mSv/MBq.

These combined results suggest that $^{68}$Ga-NODAGA-GSAO may be a promising agent for in vivo imaging of dead and dying cells and first in human studies are warranted.

Example 6

Human Studies

The following patients were administered between 200 and 207 MBq 200 MBq of $^{68}$Ga-NODAGA-GSAO:
1. 66 year old male patient with squamous cell carcinoma of the oesophagus
2. 73 year old female with metastatic ovarian carcinoma
3. 66 year old male with metastatic cutaneous squamous cell carcinoma
4. 81 year old female with invasive ductal breast carcinoma All subjects tolerated the study well with no related or unrelated serious adverse events or adverse events. There were no significant changes in any clinical, laboratory or electrocardiographic parameters.

Biodistribution

The biodistribution data demonstrates prompt intravascular distribution of $^{68}$Ga-NODAGA-GSAO with rapid initial clearance, followed by a second slower phase of clearance from the blood pool. There is rapid renal uptake and excretion.

Figure 7:
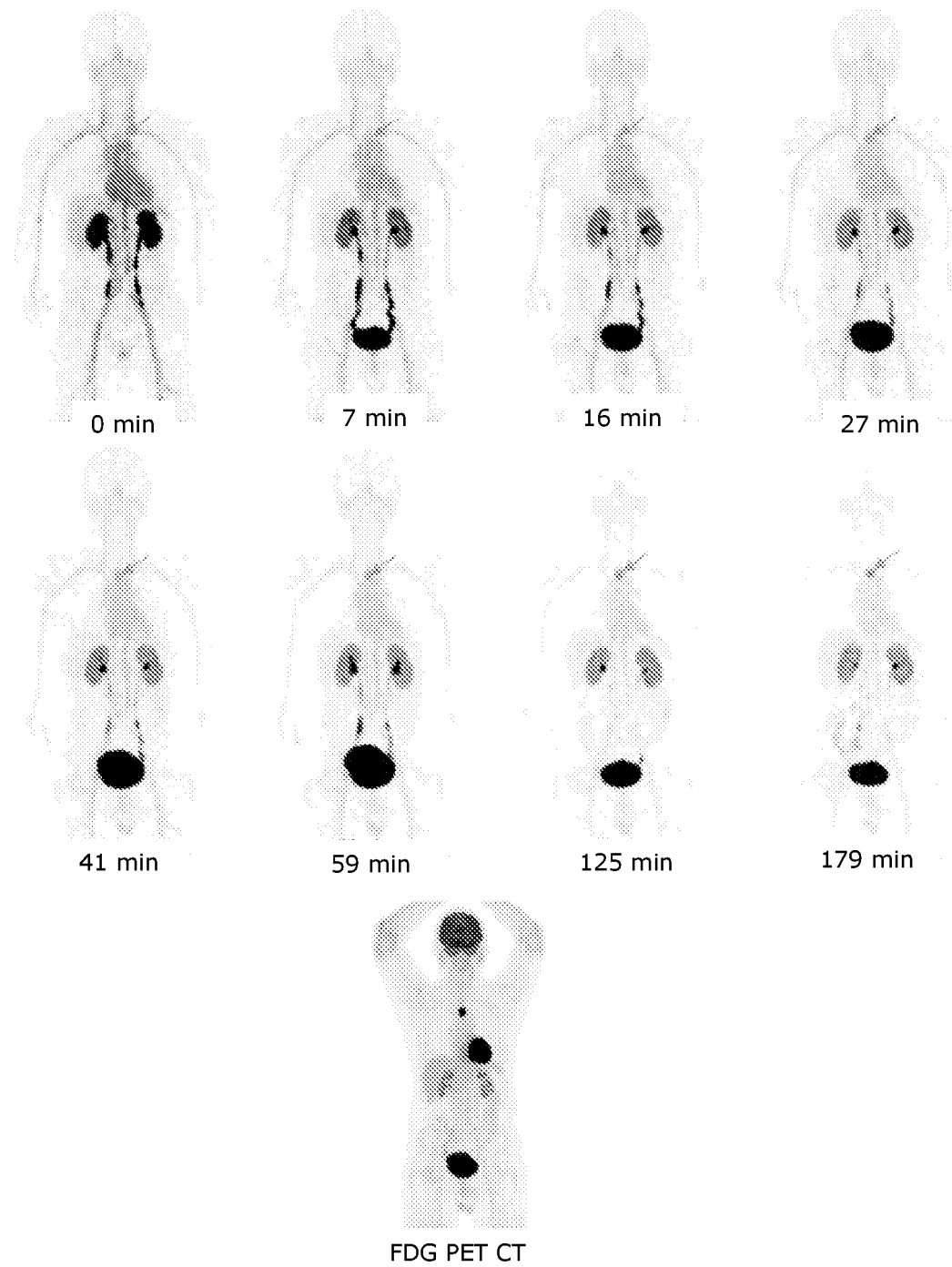
FIG. 7 shows anterior maximum intensity projections of $^{68}$Ga-NODAGA-GSAO PET at 8 time points following injection in patient 1.
Figure 8:
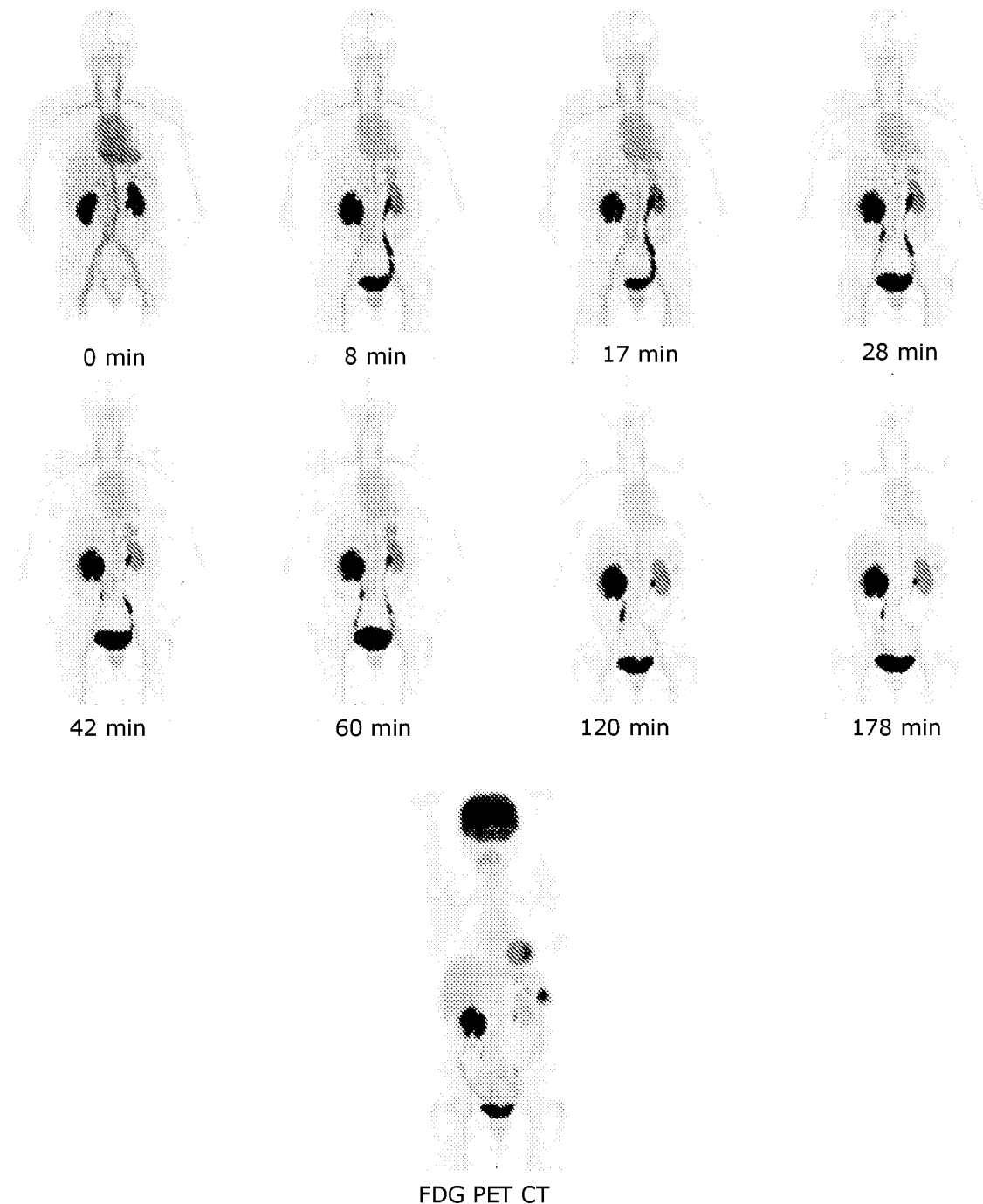
FIG. 8 shows anterior maximum intensity projections of $^{68}$Ga-NODAGA-GSAO PET at 8 time points following injection in patient 2.
Figure 9:
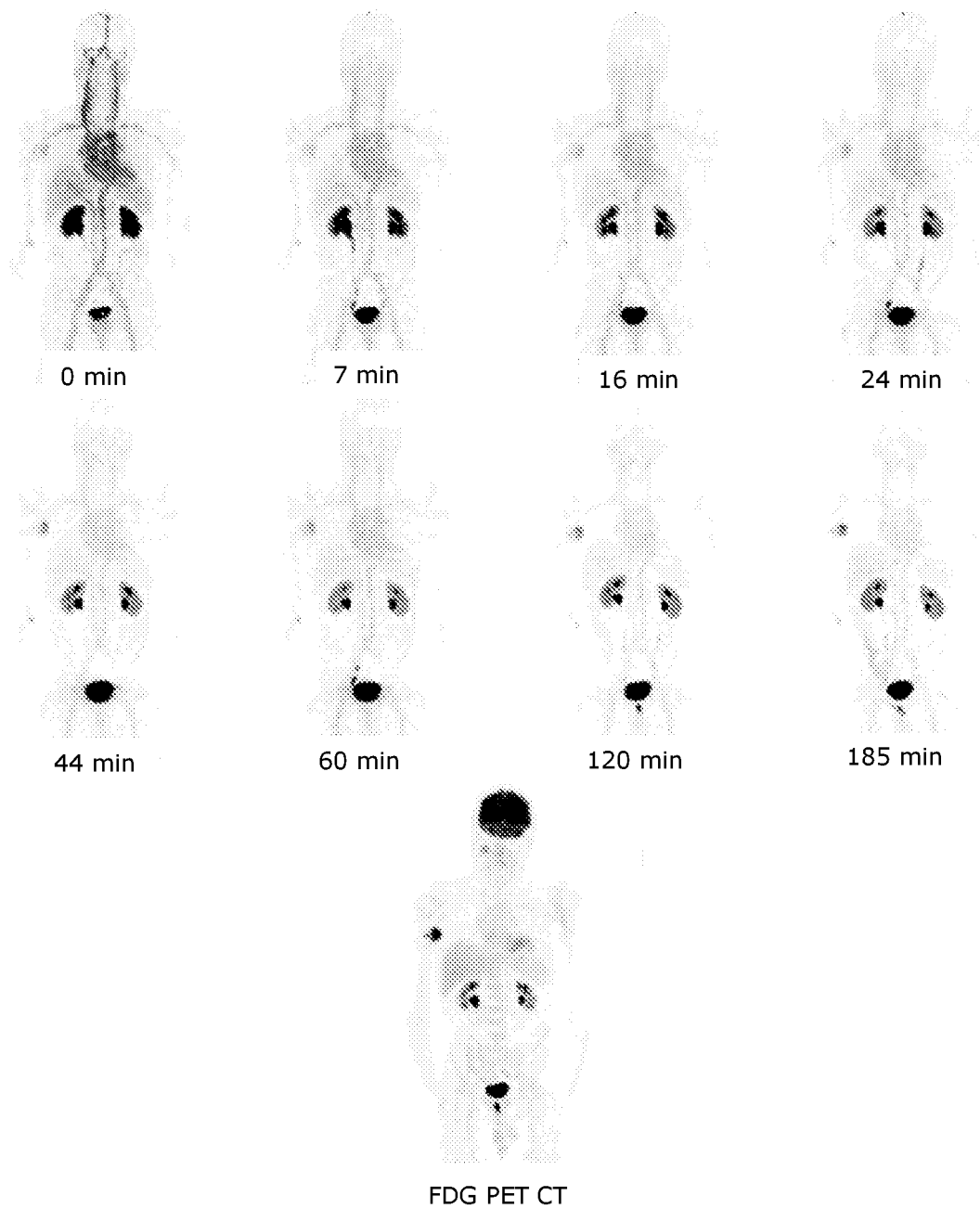
FIG. 9 shows anterior maximum intensity projections of $^{68}$Ga-NODAGA-GSAO PET at 8 time points following injection in patient 3.
Figure 10:
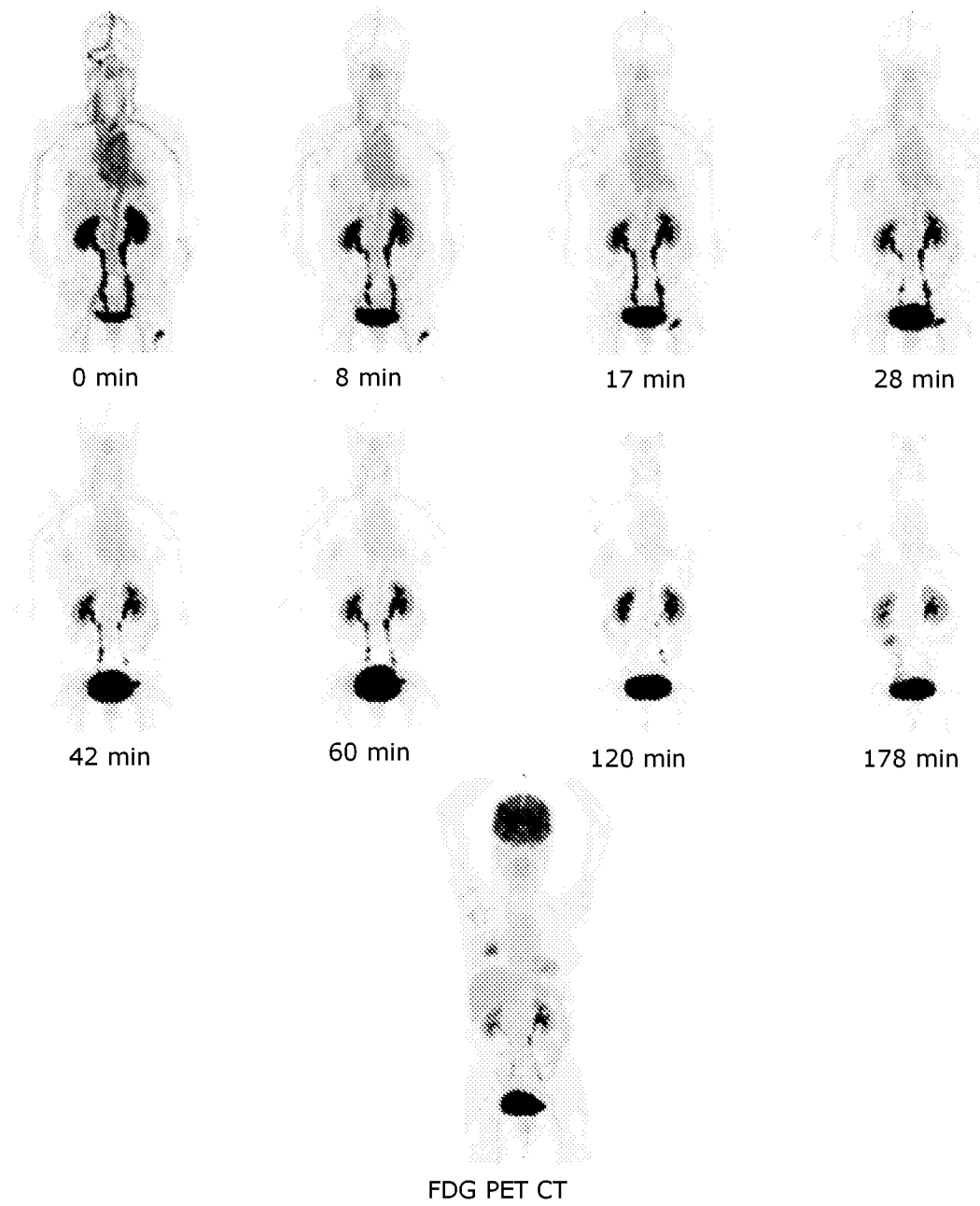
FIG. 10 shows anterior maximum intensity projections of $^{68}$Ga-NODAGA-GSAO PET at 8 time points following injection in patient 4.

For patient 1), the % injected dose (% ID) excreted in urine by 2 hours averaged 30% (range 19-38%) and by 3 hours averaged 48% (range 21-71%). Imaging findings from this subject are shown in FIG. 7, which shows anterior maximum intensity projections of $^{68}$Ga-NODAGA-GSAO PET at 8 time points; anterior maximum projection of the FDG PET is shown underneath for comparison. The location of the tumour is arrowed at each time point. Low levels of tracer uptake are seen in the remaining organs which gradually declines over time (apart from the testis and large bowel). No hepatobiliary excretion is evident. There is almost absent activity within the brain, suggesting that it does not cross the blood brain barrier to any extent. Imaging finding from patients 2-4 are similarly shown in FIG. 8 (patient 2) FIG. 9 (patient 3), FIG. 10 (patient 4).

Figure 11:
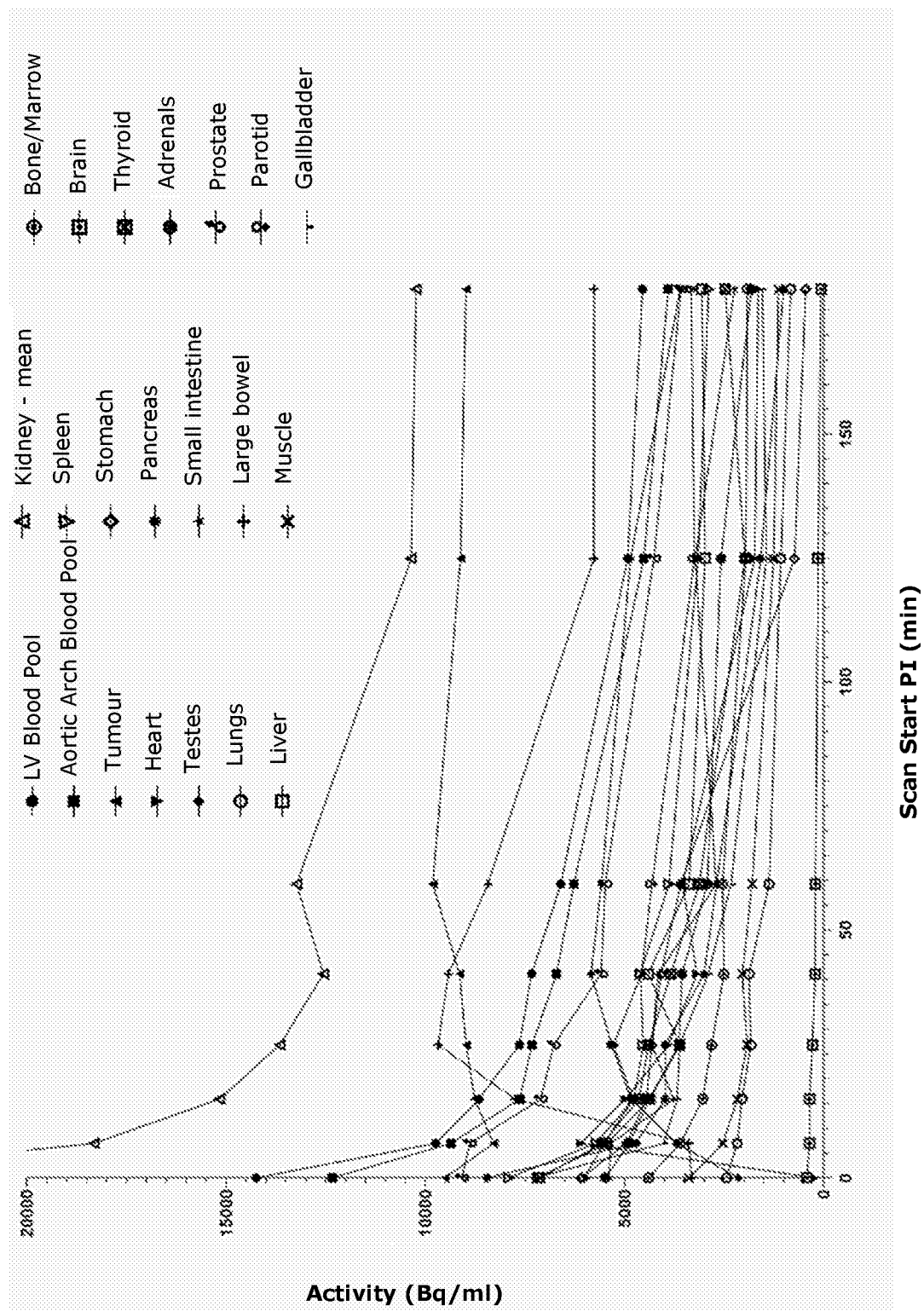
FIG. 11 shows biodistribution of $^{68}$Ga-NODAGA-GSAO in normal organs of patient 1 over time.
Figure 12:
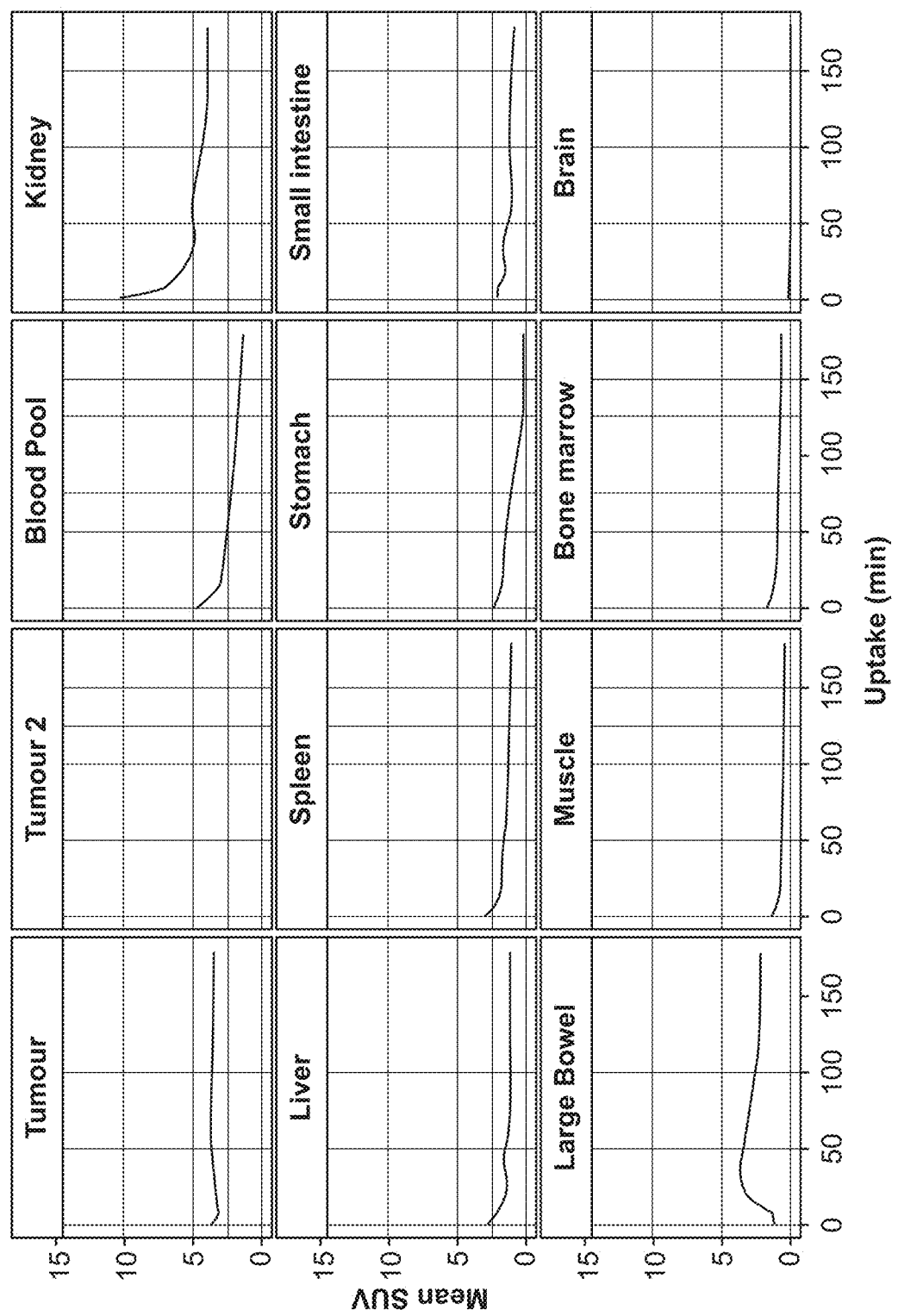
FIG. 12 shows biodistribution of $^{68}$Ga NODAGA GSAO in selected normal tissues and tumour for patient 1.
Figure 13:
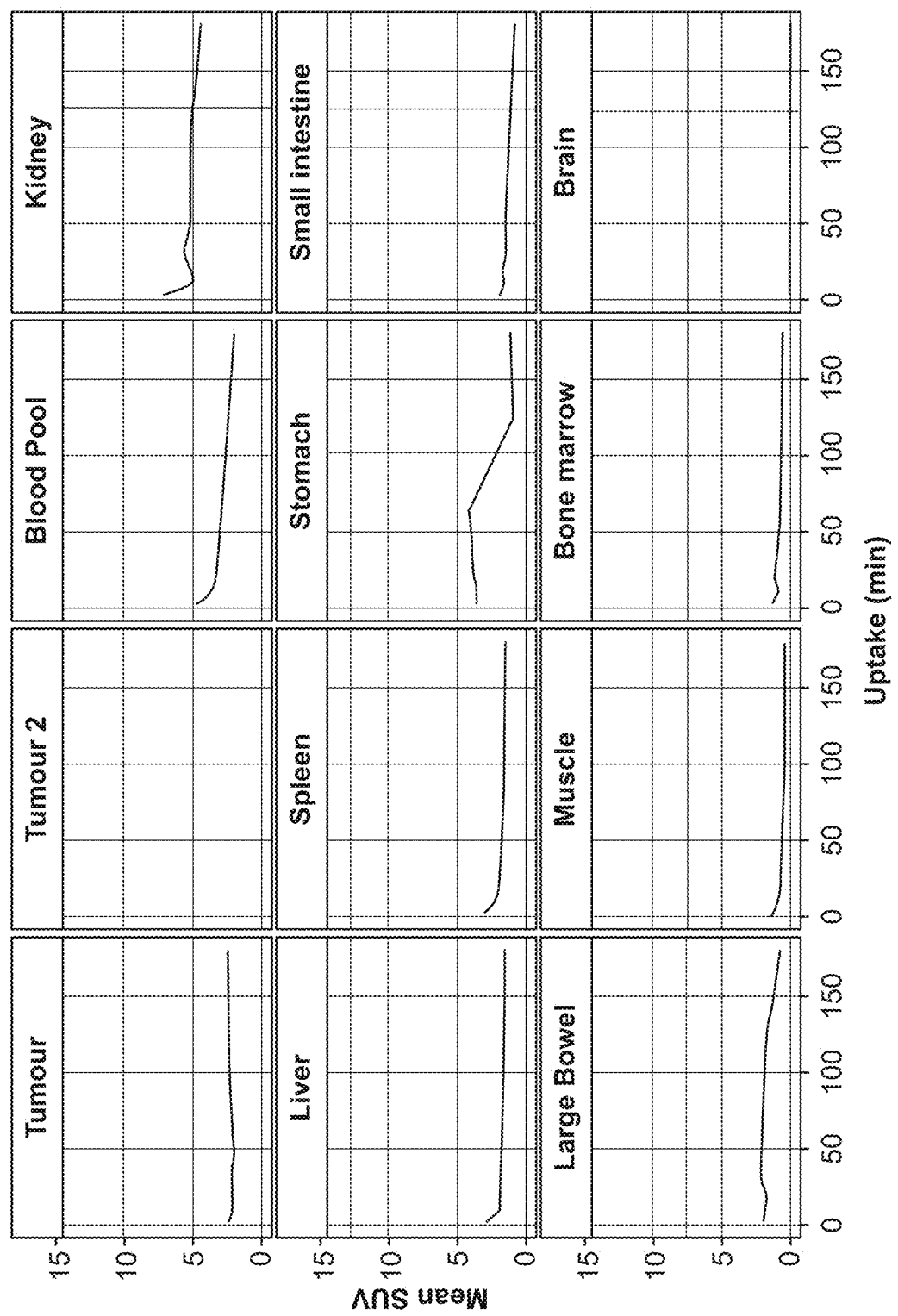
FIG. 13 shows biodistribution of $^{68}$Ga NODAGA GSAO in selected normal tissues and tumour for patient 2.
Figure 14:
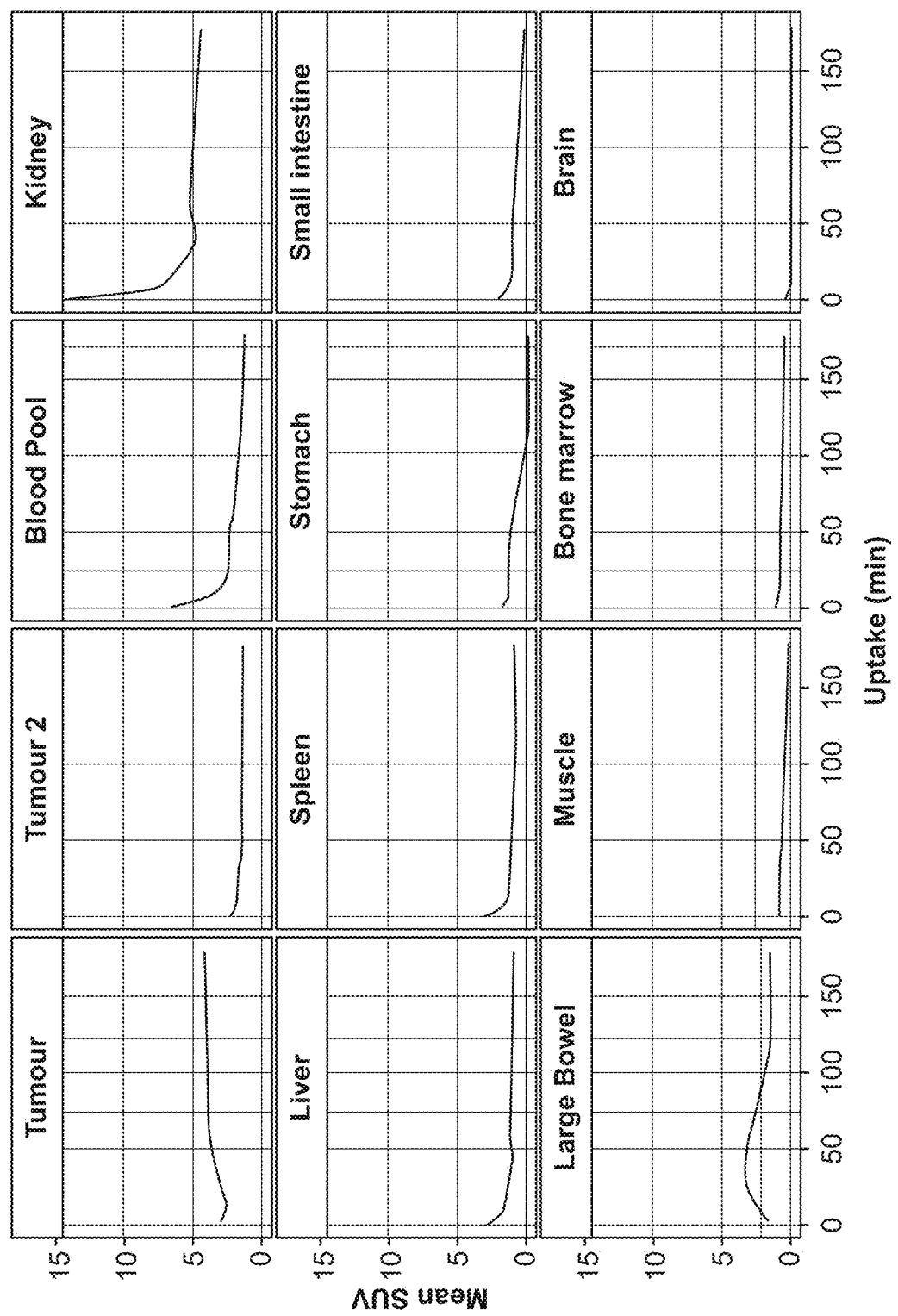
FIG. 14 shows biodistribution of $^{68}$Ga NODAGA GSAO in selected normal tissues and tumour for patient 3.
Figure 15:
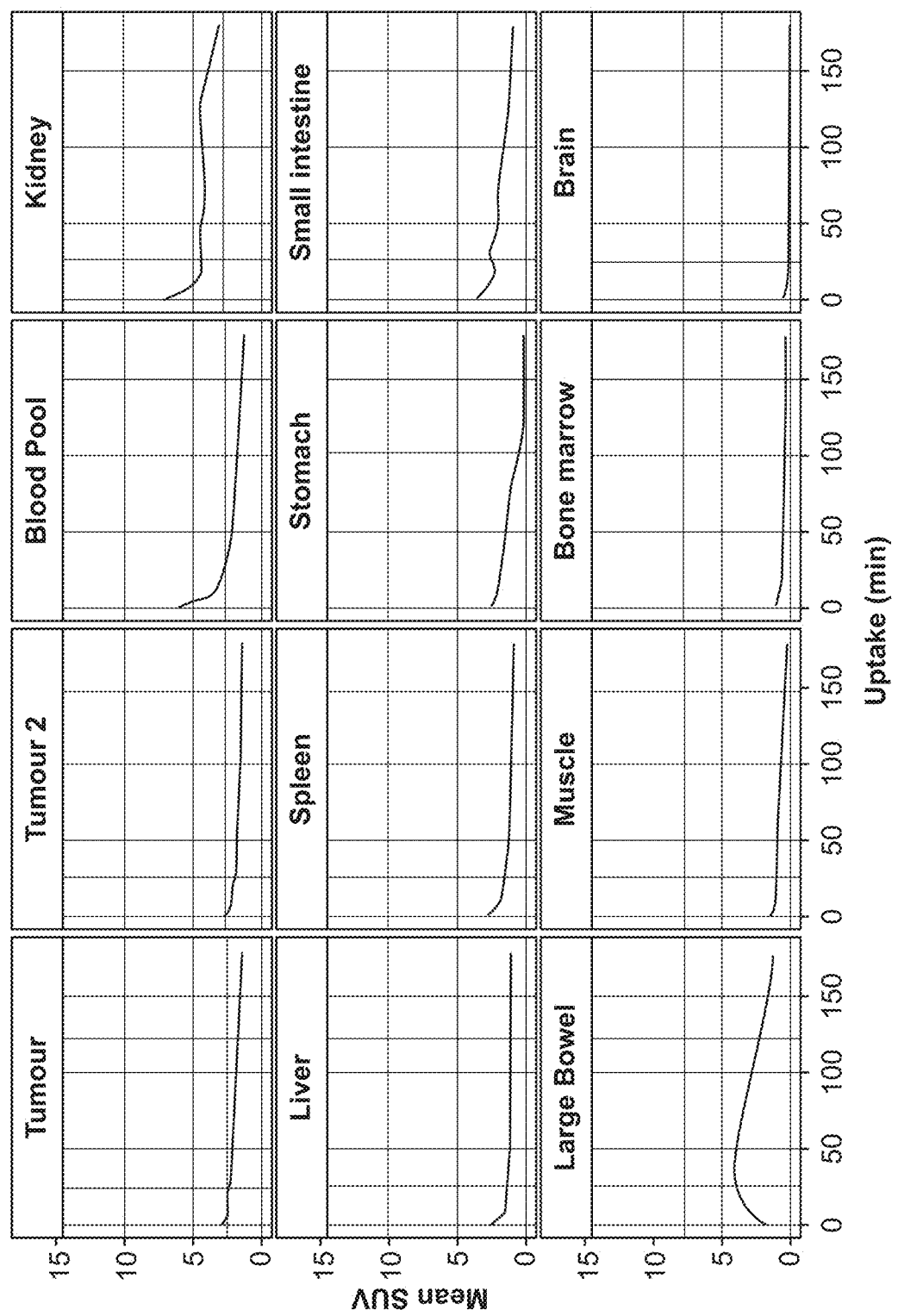
FIG. 15 shows biodistribution of $^{68}$Ga NODAGA GSAO in selected normal tissues and tumour for patient 4.

FIG. 11 shows biodistribution of $^{68}$Ga-NODAGA-GSAO in normal organs over time in patient 1. In blood there is an initial rapid decrease in concentration, followed by a second slower phase of clearance. Most of the organs demonstrate an early peak followed by a gradual decline, similar to the second phase of blood clearance, except for the large bowel and testes which demonstrate an initial increase in concentration up to approximately 40 minutes following administration and then a slow decline. This may be due to higher physiologic rates of cell death in these two organs. Note that the urinary bladder wall was evaluated separately.

Figure 16:
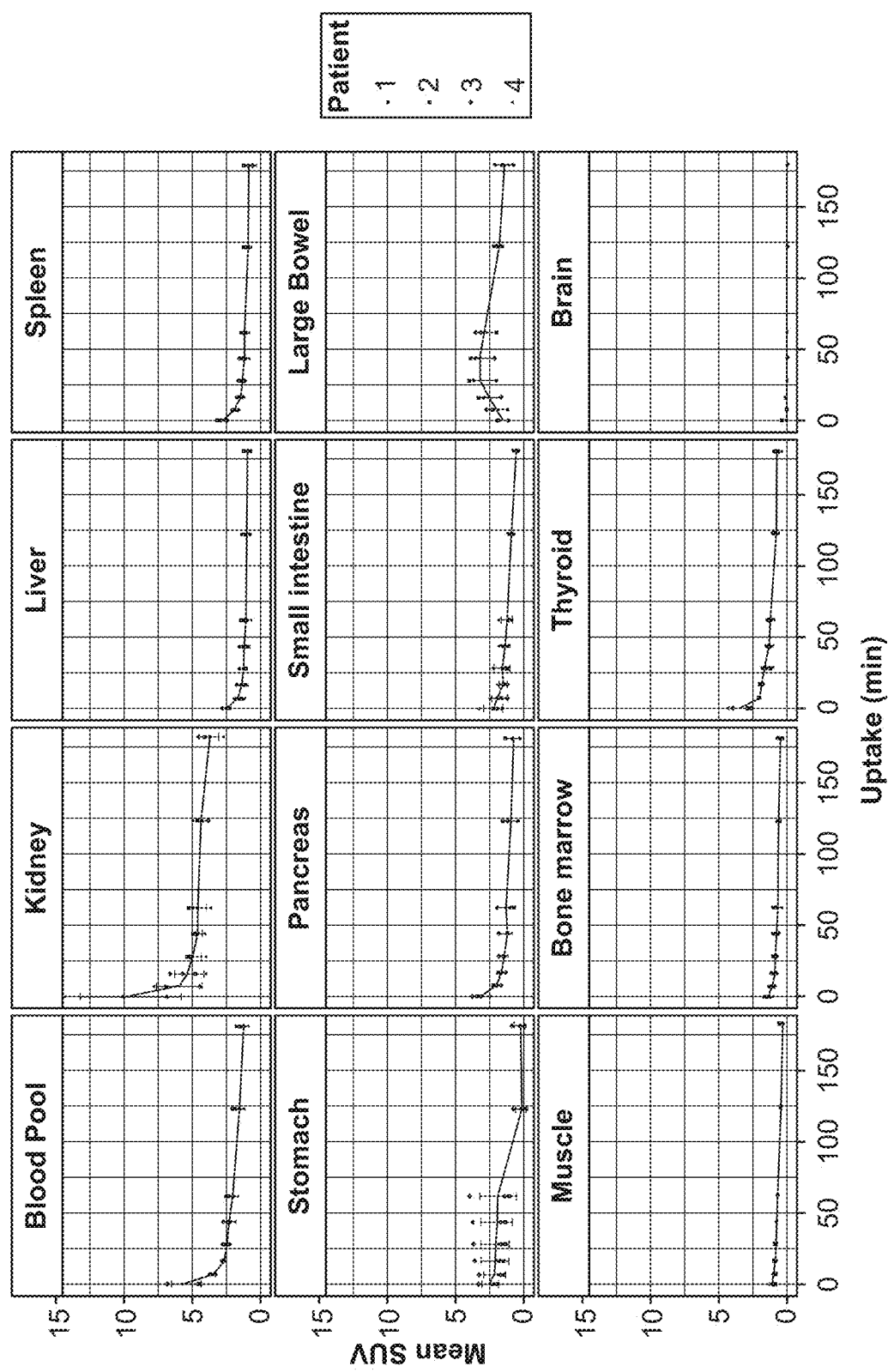
FIG. 16 shows the biodistribution in selected normal tissues (mean SUV±SD) of $^{68}$Ga NODAGA GSAO in subjects 1-4.

Patterns of biodistribution in organs and tissues were consistent across subjects 1-4 (as shown in FIG. 16). All demonstrated rapid distribution of $^{68}$Ga NODAGA GSAO through the blood pool following injection, with rapid renal uptake and excretion. At 1 h post injection, the kidneys had the highest concentration of $^{68}$Ga NODAGA GSAO (4.85±0.70; mean SUV±SD, SUV=Standard Uptake Value) with relatively low levels of $^{68}$Ga NODAGA GSAO in the other tissues and organs, which cleared over time. The large bowel has the next highest concentration of $^{68}$Ga NODAGA GSAO (3.00±0.62), followed by the blood pool (2.31±0.37) and stomach (2.05±1.34).

FIGS. 12-15 show biodistribution of $^{68}$Ga NODAGA GSAO in selected normal tissues and tumour for patients 1-4 respectively. Note that Tumour 2 is only applicable in patients 3 and 4, so is blank in FIGS. 12 and 13. FIG. 16 shows the biodistribution in selected normal tissues (mean SUV±SD) of subjects 1-4.

Radiation Dosimetry

The whole-body effective dose was estimated by drawing representative spherical volumes of interest within the organs, estimating the % ID/g for each organ and then calculating the % ID/organ using the organ weights from a standard adult phantom.

The effective whole-body dose from $^{68}$Ga NODAGA GSAO for subjects 1-4 ranged from $2.16 \times 10^{-2}$ to $3.38 \times 10^{-2}$ mSv/MBq, giving an estimated effective whole-body dose ranging from 13.5-15.9 mSv for the protocol used in the first in human study. Detailed organ dosimetry for $^{68}$Ga NODAGA GSAO is shown for the four subjects (tables 5-8). In all cases, the urinary bladder was the dose limiting organ. For subsequent human studies, fewer time points will be required, reducing the need for low dose CTs which will reduce the overall radiation dose. The dose is at level that is comparable to many routine medical imaging procedures using ionising radiation including x-ray computed tomography (CT), SPECT/CT and PET/CT scans.

For subjects 1-4, radiation dosimetry was calculated using Olinda/EXM based on the organ biodistribution discussed above. Urinary excretion was modelled based on measurement of activity in collected urine samples and urinary volume was measured from the images.

Tables 3-6 show the estimate for radiation dosimetry for subjects 1-4 of 200 MBq of $^{68}$Ga NODAGA GSAO for individual organs and for the whole body in mSv/MBq (EDE cont.=effective dose equivalent contribution, ED Cont.=effective dose contribution). The estimated whole-body dose from the one (1) low dose CT and two (2) ultra-low dose CTs was 9.2 mSv.

Table 3 shows the estimate for radiation dosimetry for subject 1. The overall estimated radiation dose to subject 1 was 14.5 mSv.

TABLE 3

| Target Organ | Alpha | Beta | Photon | Total | EDE Cont. | ED Cont. |
|---|---|---|---|---|---|---|
| Adrenals | 0.00E+00 | 9.68E−03 | 4.52E−03 | 1.42E−02 | 2.68E−04 | 7.09E−05 |
| Brain | 0.00E+00 | 6.82E−04 | 1.14E−03 | 1.82E−03 | 0.00E+00 | 9.10E−06 |
| Breasts | 0.00E+00 | 5.07E−03 | 2.11E−03 | 7.16E−03 | 1.08E−03 | 3.59E−04 |
| Gallbladder Wall | 0.00E+00 | 3.48E−03 | 4.59E−03 | 8.07E−03 | 0.00E+00 | 0.00E+00 |
| LLI Wall | 0.00E+00 | 1.29E−02 | 7.31E−03 | 2.02E−02 | 1.03E−03 | 2.43E−03 |
| Small Intestine | 0.00E+00 | 9.17E−03 | 5.21E−03 | 1.44E−02 | 0.00E+00 | 7.19E−05 |
| Stomach Wall | 0.00E+00 | 6.13E−03 | 3.93E−03 | 1.01E−02 | 0.00E+00 | 1.21E−03 |
| ULI Wall | 0.00E+00 | 7.04E−03 | 5.20E−03 | 1.22E−02 | 0.00E+00 | 6.12E−05 |
| Heart Wall | 0.00E+00 | 6.65E−03 | 3.57E−03 | 1.02E−02 | 0.00E+00 | 0.00E+00 |
| Kidneys | 0.00E+00 | 4.32E−02 | 7.22E−03 | 5.04E−02 | 3.03E−03 | 2.52E−04 |
| Liver | 0.00E+00 | 1.27E−02 | 4.84E−03 | 1.76E−02 | 5.09E−04 | 8.78E−04 |
| Lungs | 0.00E+00 | 5.19E−03 | 2.93E−03 | 8.12E−03 | 9.74E−04 | 9.74E−04 |
| Muscle | 0.00E+00 | 6.19E−03 | 3.51E−03 | 9.71E−03 | 0.00E+00 | 4.85E−05 |
| Ovaries | 0.00E+00 | 3.15E−03 | 7.00E−03 | 1.01E−02 | 1.50E−03 | 1.20E−03 |
| Pancreas | 0.00E+00 | 1.20E−02 | 4.90E−03 | 1.69E−02 | 8.14E−04 | 8.46E−05 |
| Red Marrow | 0.00E+00 | 5.39E−03 | 3.70E−03 | 9.08E−03 | 1.09E−03 | 1.09E−03 |
| Osteogenic Cells | 0.00E+00 | 7.79E−03 | 3.47E−03 | 1.12E−02 | 3.38E−04 | 1.12E−04 |
| Skin | 0.00E+00 | 3.15E−03 | 2.03E−03 | 5.17E−03 | 0.00E+00 | 5.17E−05 |
| Spleen | 0.00E+00 | 1.27E−02 | 4.57E−03 | 1.73E−02 | 5.68E−04 | 8.65E−05 |
| Testes | 0.00E+00 | 1.37E−02 | 4.58E−03 | 1.83E−02 | 4.56E−03 | 3.65E−03 |
| Thymus | 0.00E+00 | 3.15E−03 | 2.96E−03 | 6.11E−03 | 0.00E+00 | 3.06E−05 |
| Thyroid | 0.00E+00 | 1.12E−02 | 2.86E−03 | 1.41E−02 | 4.23E−04 | 7.05E−04 |
| Urinary Bladder Wall | 0.00E+00 | 2.52E−01 | 4.05E−02 | 2.93E−01 | 1.76E−02 | 1.46E−02 |
| Uterus | 0.00E+00 | 8.21E−03 | 1.06E−02 | 1.89E−02 | 5.83E−04 | 9.43E−05 |
| Total Body | 0.00E+00 | 6.33E−03 | 3.44E−03 | 9.78E−03 | 0.00E+00 | 0.00E+00 |
| Effective Dose | | | | | | 2.63E−02 |

Table 4 shows the estimate for radiation dosimetry for subject 2. The overall estimated radiation dose to subject 2 was 13.9 mSv.

TABLE 4

| Target Organ | Alpha | Beta | Photon | Total | EDE Cont | ED Cont |
|---|---|---|---|---|---|---|
| Adrenals | 0.00E+00 | 9.53E−03 | 5.24E−03 | 1.48E−02 | 0.00E+00 | 7.38E−05 |
| Brain | 0.00E+00 | 6.40E−04 | 1.46E−03 | 2.10E−03 | 0.00E+00 | 1.05E−05 |
| Breasts | 0.00E+00 | 9.48E−03 | 2.76E−03 | 1.22E−02 | 1.84E−03 | 6.12E−04 |
| Gallbladder Wall | 0.00E+00 | 4.69E−03 | 5.27E−03 | 9.96E−03 | 0.00E+00 | 0.00E+00 |
| LLI Wall | 0.00E+00 | 1.37E−02 | 7.16E−03 | 2.08E−02 | 1.25E−03 | 2.50E−03 |
| Small Intestine | 0.00E+00 | 1.27E−02 | 5.57E−03 | 1.83E−02 | 0.00E+00 | 9.14E−05 |
| Stomach Wall | 0.00E+00 | 1.15E−02 | 4.97E−03 | 1.65E−02 | 0.00E+00 | 1.98E−03 |
| ULI Wall | 0.00E+00 | 1.19E−02 | 6.02E−03 | 1.79E−02 | 0.00E+00 | 8.97E−05 |
| Heart Wall | 0.00E+00 | 8.27E−03 | 4.29E−03 | 1.26E−02 | 0.00E+00 | 0.00E+00 |
| Kidneys | 0.00E+00 | 4.21E−02 | 7.59E−03 | 4.97E−02 | 2.98E−03 | 2.48E−04 |
| Liver | 0.00E+00 | 1.45E−02 | 5.51E−03 | 2.00E−02 | 0.00E+00 | 1.00E−03 |

TABLE 4-continued

| Target Organ | Alpha | Beta | Photon | Total | EDE Cont | ED Cont |
|---|---|---|---|---|---|---|
| Lungs | 0.00E+00 | 5.73E-03 | 3.54E-03 | 9.27E-03 | 1.11E-03 | 1.11E-03 |
| Muscle | 0.00E+00 | 6.08E-03 | 3.83E-03 | 9.91E-03 | 0.00E+00 | 4.95E-05 |
| Ovaries | 0.00E+00 | 4.69E-03 | 6.95E-03 | 1.16E-02 | 2.91E-03 | 2.33E-03 |
| Pancreas | 0.00E+00 | 1.62E-02 | 5.90E-03 | 2.21E-02 | 1.32E-03 | 1.10E-04 |
| Red Marrow | 0.00E+00 | 6.61E-03 | 4.24E-03 | 1.08E-02 | 1.30E-03 | 1.30E-03 |
| Osteogenic Cells | 0.00E+00 | 1.14E-02 | 4.14E-03 | 1.55E-02 | 4.65E-04 | 1.55E-04 |
| Skin | 0.00E+00 | 4.69E-03 | 2.32E-03 | 7.01E-03 | 0.00E+00 | 7.01E-05 |
| Spleen | 0.00E+00 | 1.48E-02 | 5.34E-03 | 2.02E-02 | 1.21E-03 | 1.01E-04 |
| Thymus | 0.00E+00 | 4.69E-03 | 3.66E-03 | 8.36E-03 | 0.00E+00 | 4.18E-05 |
| Thyroid | 0.00E+00 | 1.19E-02 | 3.24E-03 | 1.52E-02 | 4.55E-04 | 7.59E-04 |
| Urinary Bladder Wall | 0.00E+00 | 1.84E-01 | 3.21E-02 | 2.16E-01 | 1.30E-02 | 1.08E-02 |
| Uterus | 0.00E+00 | 4.69E-03 | 8.98E-03 | 1.37E-02 | 0.00E+00 | 6.84E-05 |
| Total Body | 0.00E+00 | 7.76E-03 | 3.84E-03 | 1.16E-02 | 0.00E+00 | 0.00E+00 |
| Effective Dose | | | | | | 2.35E-02 |

Table 5 shows the estimate for radiation dosimetry for subject 3. The overall estimated radiation dose to subject 3 was 13.5 mSv.

Table 6 shows the estimate for radiation dosimetry for subject 4. The overall estimated radiation dose to subject 4 was 15.9 mSv.

TABLE 5

| Target Organ | | | | | EDE Cont. | ED Cont. |
|---|---|---|---|---|---|---|
| Adrenals | 0.00E+00 | 5.97E-03 | 3.71E-03 | 9.68E-03 | 0.00E+00 | 4.84E-05 |
| Brain | 0.00E+00 | 6.13E-04 | 8.65E-04 | 1.48E-03 | 0.00E+00 | 7.39E-06 |
| Breasts | 0.00E+00 | 2.02E-03 | 1.59E-03 | 3.61E-03 | 5.41E-04 | 1.80E-04 |
| Gallbladder Wall | 0.00E+00 | 2.02E-03 | 4.07E-03 | 6.09E-03 | 0.00E+00 | 0.00E+00 |
| LLI Wall | 0.00E+00 | 1.44E-02 | 5.96E-03 | 2.03E-02 | 1.22E-03 | 2.44E-03 |
| Small Intestine | 0.00E+00 | 8.73E-03 | 4.29E-03 | 1.30E-02 | 0.00E+00 | 6.51E-05 |
| Stomach Wall | 0.00E+00 | 4.31E-03 | 3.12E-03 | 7.43E-03 | 0.00E+00 | 8.91E-04 |
| ULI Wall | 0.00E+00 | 2.02E-03 | 4.00E-03 | 6.02E-03 | 0.00E+00 | 3.01E-05 |
| Heart Wall | 0.00E+00 | 4.65E-03 | 2.82E-03 | 7.48E-03 | 0.00E+00 | 0.00E+00 |
| Kidneys | 0.00E+00 | 4.45E-02 | 6.83E-03 | 5.13E-02 | 3.08E-03 | 2.57E-04 |
| Liver | 0.00E+00 | 1.20E-02 | 4.36E-03 | 1.64E-02 | 9.84E-04 | 8.20E-04 |
| Lungs | 0.00E+00 | 5.16E-03 | 2.37E-03 | 7.53E-03 | 9.04E-04 | 9.04E-04 |
| Muscle | 0.00E+00 | 5.15E-03 | 2.83E-03 | 7.98E-03 | 0.00E+00 | 3.99E-05 |
| Ovaries | 0.00E+00 | 2.02E-03 | 5.52E-03 | 7.54E-03 | 0.00E+00 | 0.00E+00 |
| Pancreas | 0.00E+00 | 1.13E-02 | 4.18E-03 | 1.54E-02 | 9.27E-04 | 7.72E-05 |
| Red Marrow | 0.00E+00 | 4.29E-03 | 2.96E-03 | 7.25E-03 | 8.70E-04 | 8.70E-04 |
| Osteogenic Cells | 0.00E+00 | 4.95E-03 | 2.74E-03 | 7.69E-03 | 2.31E-04 | 7.69E-05 |
| Skin | 0.00E+00 | 2.02E-03 | 1.63E-03 | 3.66E-03 | 0.00E+00 | 3.66E-05 |
| Spleen | 0.00E+00 | 1.09E-02 | 3.83E-03 | 1.47E-02 | 0.00E+00 | 7.35E-05 |
| Testes | 0.00E+00 | 1.22E-02 | 4.18E-03 | 1.64E-02 | 4.09E-03 | 3.27E-03 |
| Thymus | 0.00E+00 | 2.02E-03 | 2.30E-03 | 4.32E-03 | 0.00E+00 | 2.16E-05 |
| Thyroid | 0.00E+00 | 8.46E-03 | 2.38E-03 | 1.08E-02 | 3.25E-04 | 5.42E-04 |
| Urinary Bladder Wall | 0.00E+00 | 1.91E-01 | 2.79E-02 | 2.19E-01 | 1.31E-02 | 1.09E-02 |
| Uterus | 0.00E+00 | 2.02E-03 | 8.36E-03 | 1.04E-02 | 0.00E+00 | 5.19E-05 |
| Total Body | 0.00E+00 | 4.94E-03 | 2.77E-03 | 7.71E-03 | 0.00E+00 | 0.00E+00 |
| Effective Dose | | | | | | 2.16E-02 |

TABLE 6

| Target Organ | Alpha | Beta | Photon | Total | EDE Cont. | ED Cont. |
|---|---|---|---|---|---|---|
| Adrenals | 0.00E+00 | 1.30E−02 | 4.86E−03 | 1.79E−02 | 1.07E−03 | 8.93E−05 |
| Brain | 0.00E+00 | 7.79E−04 | 1.23E−03 | 2.01E−03 | 0.00E+00 | 1.00E−05 |
| Breasts | 0.00E+00 | 6.43E−03 | 2.25E−03 | 8.68E−03 | 1.30E−03 | 4.34E−04 |
| Gallbladder Wall | 0.00E+00 | 4.09E−03 | 4.46E−03 | 8.56E−03 | 0.00E+00 | 0.00E+00 |
| LLI Wall | 0.00E+00 | 3.53E−03 | 8.79E−03 | 1.23E−02 | 0.00E+00 | 1.48E−03 |
| Small Intestine | 0.00E+00 | 3.53E−03 | 5.67E−03 | 9.20E−03 | 0.00E+00 | 4.60E−05 |
| Stomach Wall | 0.00E+00 | 3.53E−03 | 4.01E−03 | 7.54E−03 | 0.00E+00 | 9.05E−04 |
| ULI Wall | 0.00E+00 | 3.53E−03 | 5.50E−03 | 9.03E−03 | 0.00E+00 | 4.52E−05 |
| Heart Wall | 0.00E+00 | 7.57E−03 | 3.84E−03 | 1.14E−02 | 0.00E+00 | 0.00E+00 |
| Kidneys | 0.00E+00 | 4.30E−02 | 7.33E−03 | 5.03E−02 | 3.02E−03 | 2.52E−04 |
| Liver | 0.00E+00 | 1.16E−02 | 4.71E−03 | 1.63E−02 | 0.00E+00 | 8.13E−04 |
| Lungs | 0.00E+00 | 4.82E−03 | 3.15E−03 | 7.97E−03 | 9.57E−04 | 9.57E−04 |
| Muscle | 0.00E+00 | 7.68E−03 | 4.07E−03 | 1.18E−02 | 0.00E+00 | 5.88E−05 |
| Ovaries | 0.00E+00 | 3.53E−03 | 8.79E−03 | 1.23E−02 | 3.08E−03 | 2.46E−03 |
| Pancreas | 0.00E+00 | 1.18E−02 | 5.04E−03 | 1.69E−02 | 1.01E−03 | 8.44E−05 |
| Red Marrow | 0.00E+00 | 5.25E−03 | 4.13E−03 | 9.38E−03 | 1.13E−03 | 1.13E−03 |
| Osteogenic Cells | 0.00E+00 | 8.81E−03 | 3.80E−03 | 1.26E−02 | 3.78E−04 | 1.26E−04 |
| Skin | 0.00E+00 | 3.53E−03 | 2.26E−03 | 5.79E−03 | 0.00E+00 | 5.79E−05 |
| Spleen | 0.00E+00 | 1.18E−02 | 4.70E−03 | 1.65E−02 | 0.00E+00 | 8.27E−05 |
| Thymus | 0.00E+00 | 3.53E−03 | 3.23E−03 | 6.76E−03 | 0.00E+00 | 3.38E−05 |
| Thyroid | 0.00E+00 | 1.34E−02 | 3.00E−03 | 1.64E−02 | 4.91E−04 | 8.18E−04 |
| Urinary Bladder Wall | 0.00E+00 | 4.06E−01 | 6.85E−02 | 4.74E−01 | 2.85E−02 | 2.37E−02 |
| Uterus | 0.00E+00 | 2.38E−02 | 1.51E−02 | 3.89E−02 | 2.33E−03 | 1.95E−04 |
| Total Body | 0.00E+00 | 6.96E−03 | 3.92E−03 | 1.09E−02 | 0.00E+00 | 0.00E+00 |
| Effective Dose | | | | | | 3.38E−02 |

Tumour Uptake

Figure 17:
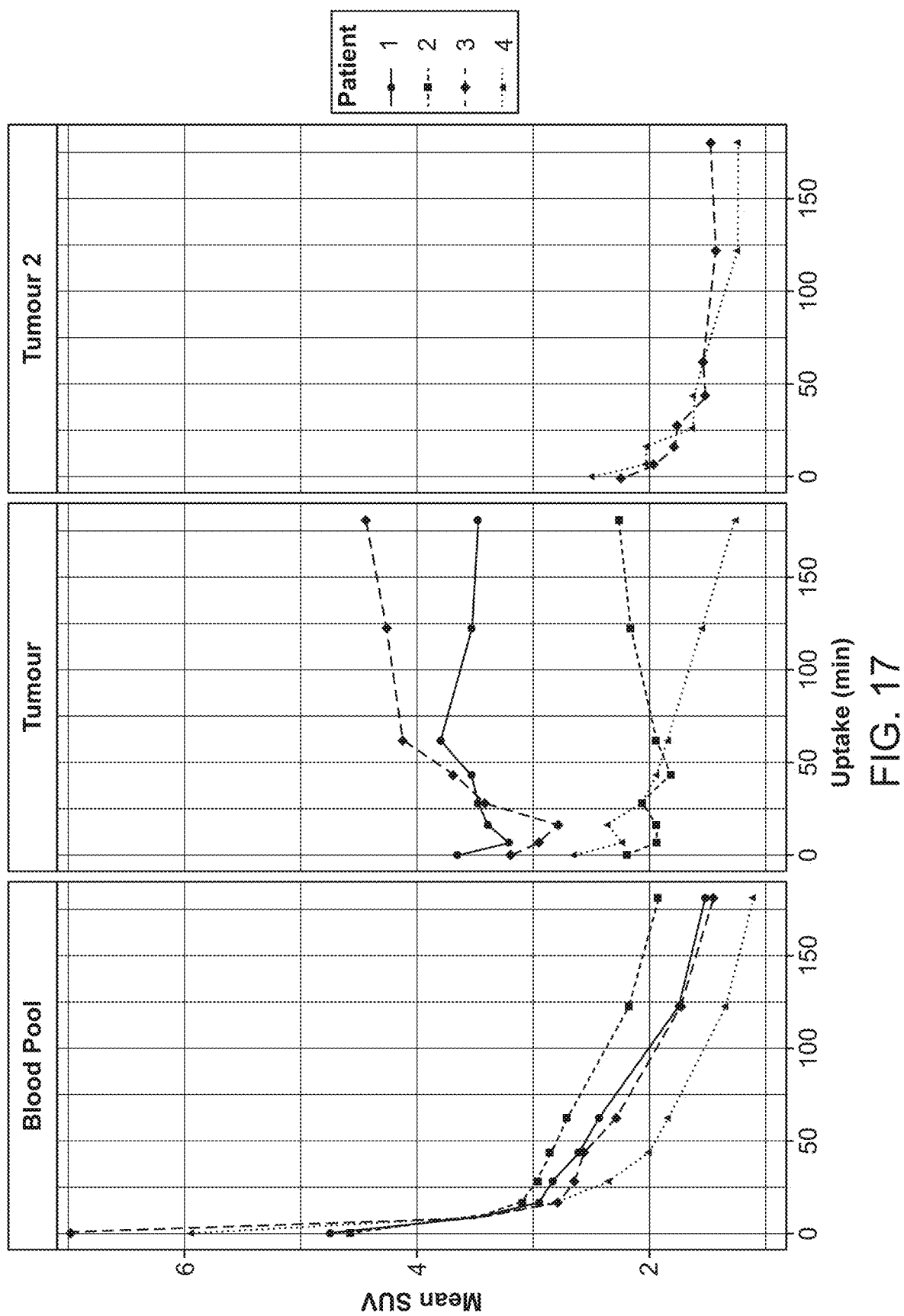
FIG. 17 shows blood pool activity and uptake of $^{68}$Ga NODAGA GSAO into tumour deposits in subjects 1-4.

FIG. 17 shows blood pool activity and uptake of $^{68}$Ga NODAGA GSAO into tumour deposits in subjects 1-4 (note: in patients 3 and 4, there are two tumour deposits, and these have been analysed separately). Whilst blood pool and clearance are reproducible, tumour uptake and clearance vary by tumour type.

Across subjects 1-4, tumour uptake was variable depending on tumour histology, with high levels of uptake seen in squamous cell carcinoma of the oesophagus (SUVmean 3.8) and metastatic cutaneous squamous cell carcinoma (SUVmean 4.1) and lower uptake seen in metastatic ovarian carcinoma (SUVmean 1.9) and breast carcinoma (SUVmean 1.8). Note that in subjects 3 and 4 there were two tumour deposits and these have been analysed separately. It is not unexpected that different tumour histology will have differing rates of de novo cell death. To confirm this, histological correlation of tumour cell death with tumour uptake of $^{68}$Ga NODAGA GSAO was performed on two tumour deposits in patient 3 (one with high uptake of $^{68}$Ga NODAGA GSAO SUVmean 4.1 in the right axilla and the other with low uptake of $^{68}$Ga NODAGA GSAO SUVmean 2.7 in the right upper anterior cervical triangle) (FIG. 18).

Dissected tumours were fixed in formalin, embedded in paraffin and 4 μm thick sections were cut. Adjacent sections were stained for apoptotic cells using TUNEL (Abcam, Cat #206386) or morphology using haematoxylin and eosin. For TUNEL staining, sections were deparaffinized in xylene, rehydrated in decreasing concentrations of ethanol and permeabilized with Proteinase K for 20 min at room temperature. The endogenous peroxidase activity was quenched with 3% $H_2O_2$ for 5 min. Apoptotic cells were labelled with biotinylated terminal deoxynucleotidyl transferase at 37° C. in a humidified chamber for 2 h followed by a 30 min incubation with streptavidin-HRP conjugate. HRP-positive cells were developed using diaminobenzidine and sections counterstained with methyl green (Sigma). Whole sections were imaged using PowerMosaic scanning at 10× magnification on a Leica DM6000D microscope.

Figure 18:
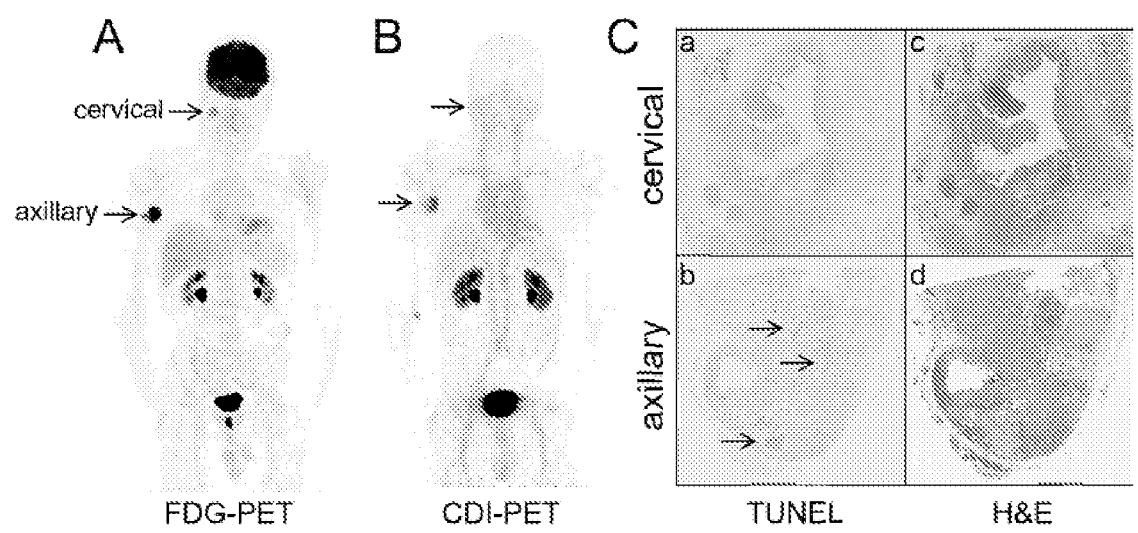
FIG. 18 shows anterior maximum projection intensity images of FDG-PET (FIG. 18A) performed 60 min after administration of 256 MBq of FDG (Fluorodeoxyglucose), and CDI-PET (FIG. 18B) performed 60 min after administration of 205 MBq of CDI (68Ga NODAGA GSAO) in patient 3. The tumours were surgically excised, fixed and adjacent sections stained for apoptotic cells (FIG. 18C, brown TUNEL stain, a and b) or for morphology by haematoxylin and eosin (FIG. 18C, c and d).

FIG. 18 shows anterior maximum projection intensity images of FDG-PET (FIG. 18A) performed 60 min after administration of 256 MBq of FDG (Fluorodeoxyglucose), and CDI-PET (FIG. 18B) performed 60 min after administration of 205 MBq of CDI ($^{68}$Ga NODAGA GSAO) in a 66 year old male with metastatic cutaneous squamous cell carcinoma (patient 3). The FDG-PET demonstrates two intensely metabolically active nodal metastases, one in the right axilla and the other in the right upper anterior cervical triangle. These are thought to represent synchronous nodal metastases from two different cutaneous squamous cell carcinomas (previously resected). The CDI-PET ($^{68}$Ga NODAGA GSAO) demonstrates intense uptake in the right axillary nodal metastasis (SUVmean=4.1) and mild uptake in the right anterior cervical triangle nodal metastasis (SUVmean=1.7). The tumours were surgically excised, fixed and adjacent sections stained for apoptotic cells (FIG. 18C, brown TUNEL stain, a and b) or for morphology by haematoxylin and eosin (FIG. 18C, c and d). Arrows in the TUNEL staining point to areas of extensive apoptosis.

Note that those tumours with high uptake have uptake up to 2 fold greater than blood pool, and the uptake is greater than uptake in all other organs except for the renal tract which is the route of excretion. This high level of uptake within some tumours combined with the low level of activity within normal tissues and organs demonstrates the potential for use of $^{68}$Ga NODAGA GSAO as an effective imaging agent.

Discussion

The interim analysis of the first four patients in this first in human study of $^{68}$Ga-NODAGA-GSAO demonstrates it is safe, well-tolerated and without adverse effects. The biodistribution and imaging characteristics are favourable with only low levels of activity in most normal organs. The urinary tract is the only route of excretion. Uptake into dead and dying cells in the tumour is seen and $^{68}$Ga-NODAGA-GSAO tumour uptake variable consistent with varying tumour histologies, and has been demonstrated histopathologically to correlate with the proportion of dead and dying cells within the tumour. The effective whole-body dose from 68Ga NODAGA GSAO ranged from $2.16 \times 10^{-2}$ to $3.38 \times 10^{-2}$ mSv/MBq, giving an estimated effective whole-body dose ranging from 4.3-6.8 mSv for ad administered activity of 200 MBq. This is comparable to many other diagnostic radiopharmaceuticals used for PET/CT and SPECT/CT as well as for effective whole-body dose from other radiologic procedures such as x-ray computed tomography (CT).

The invention claimed is:

1. A compound according to Formula (Ia)

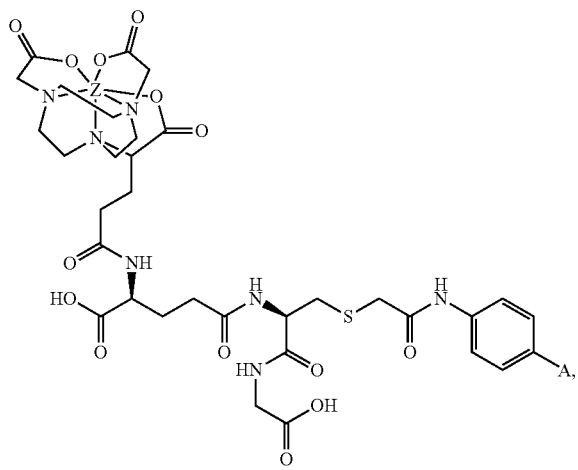

Formula (Ia)

wherein A is —As(OH)$_2$;

and Z is selected from the group consisting of $^{64}$Cu, {Al$^{18}$F}$^{2+}$, $^{68}$Ga, and $^{99m}$Tc;

or a pharmaceutically acceptable salt or solvate thereof.

2. The compound according to claim 1, wherein Z is $^{68}$Ga or is {Al$^{18}$F}$^{2+}$.

3. A pharmaceutical composition comprising the compound of claim 1 together with a pharmaceutically acceptable carrier, excipient, diluent, vehicle and/or adjuvant.

4. A compound according to Formula (IIa)

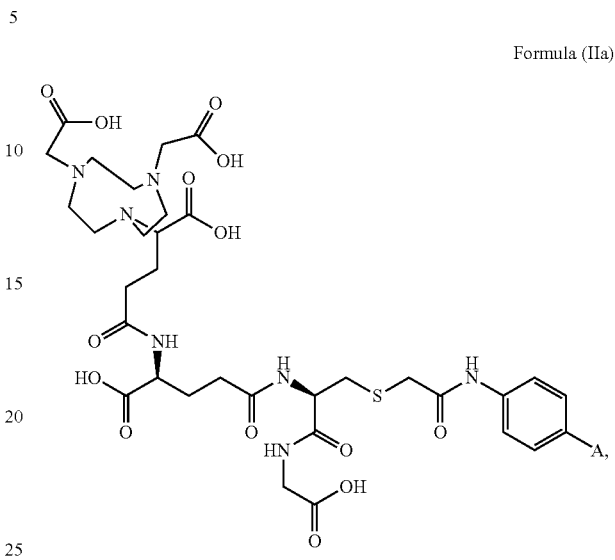

Formula (IIa)

wherein A is —As(OH)$_2$ or an arsenoxide equivalent group;

or a pharmaceutically acceptable salt, or solvate thereof.

5. A method of diagnosing or treating a condition in a subject in need thereof wherein the condition is associated with changes in cell death and/or treatment of the condition results in a change in cell death, or visualizing cell death in a subject comprising administering an effective amount of the compound according to claim 1 to said subject.

6. The method according to claim 5 wherein the condition is a neoplastic condition or an autoimmune condition.

7. The method according to claim 5, further comprising conducting positron-emission tomography on the subject following administration of the compound.

8. The method according to claim 5, wherein the compound is administered intravenously.

9. The method according to claim 6, wherein the neoplastic condition is a tumor.

10. A method of assessing response of a subject to a therapy intended to cause a change in level of cell death, comprising:

administering the therapy;

administering the compound according to claim 1; and visualizing cell death.

11. The method according to claim 10, wherein cell death is visualized by conducting positron emission tomography on the subject.

12. The method according to claim 11, wherein the therapy is chemotherapy, radiotherapy, targeted therapy or immunotherapy, or a combination thereof.

13. A process for preparing a compound according to claim 2, wherein Z is $^{68}$Ga, said process comprising eluting $^{68}$Ga onto a strong cation exchange column, and eluting the strong cation exchange column into a mixture comprising a compound according to Formula (IIa)

Formula (IIa)

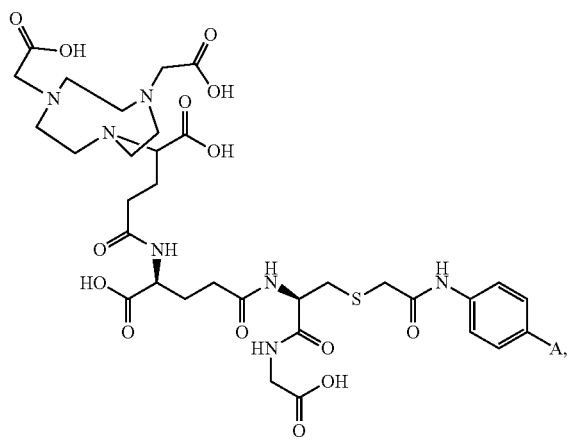

or a pharmaceutically acceptable salt thereof, and a buffer, wherein A is —As(OH)$_2$; and wherein the buffer has a pH of about 4.5.

14. The compound of claim 1, wherein Z is $^{64}$Cu.
15. The compound of claim 1, wherein Z is {Al$^{18}$F}$^{2+}$.
16. The compound of claim 1, wherein Z is $^{68}$Ga.
17. The compound of claim 1, wherein Z is $^{99m}$Tc.
18. The compound of claim 1, having the following structure:

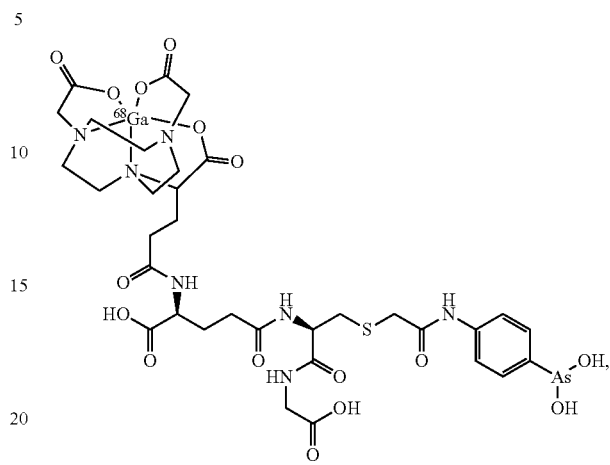

or a pharmaceutically acceptable salt thereof.

19. The compound of claim 4, having the following structure:

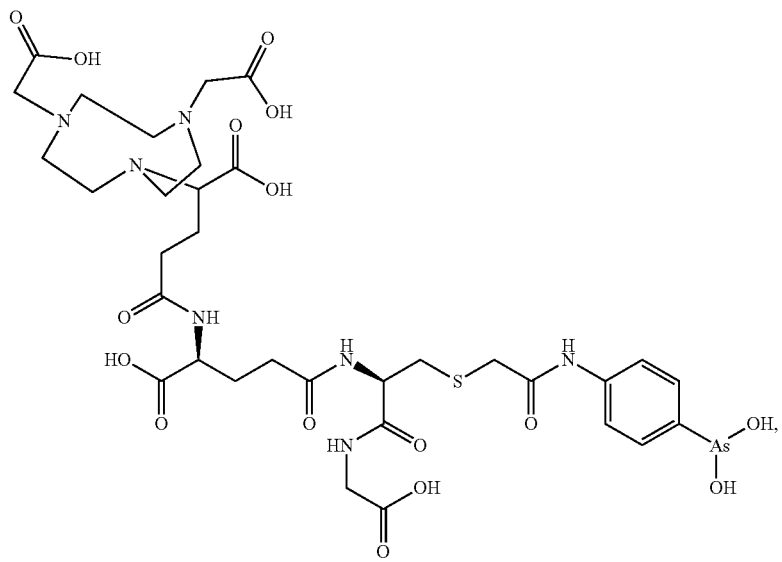

or a pharmaceutically acceptable salt thereof.

* * * * *